United States Patent
Melkent et al.

(10) Patent No.: US 8,105,339 B2
(45) Date of Patent: *Jan. 31, 2012

(54) IMAGE GUIDED SPINAL SURGERY GUIDE SYSTEM AND METHOD FOR USE THEREOF

(75) Inventors: Anthony J. Melkent, Lafayette, CO (US); Kevin T. Foley, Memphis, TN (US); Bradley T. Estes, Memphis, TN (US); Joseph Chaudoin, Germantown, TN (US)

(73) Assignee: Sofamor Danek Holdings, Inc., Broomfield, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 12/840,923

(22) Filed: Jul. 21, 2010

(65) Prior Publication Data

US 2010/0286713 A1 Nov. 11, 2010

Related U.S. Application Data

(60) Division of application No. 10/939,953, filed on Sep. 13, 2004, now Pat. No. 7,763,035, which is a continuation of application No. 09/992,546, filed on Nov. 6, 2001, now Pat. No. 6,796,988, which is a continuation of application No. 09/209,248, filed on Dec. 10, 1998, now Pat. No. 6,348,058.

(60) Provisional application No. 60/069,595, filed on Dec. 12, 1997.

(51) Int. Cl.
*A61B 19/00* (2006.01)
(52) U.S. Cl. .................... 606/130; 600/424
(58) Field of Classification Search .............. 606/61, 606/96–97, 130; 600/426–427, 429, 424
See application file for complete search history.

(56) References Cited

U.S. PATENT DOCUMENTS

| 1,576,781 | A | 3/1926 | Phillips |
| 1,735,726 | A | 11/1929 | Bornhardt |
| 2,407,845 | A | 9/1946 | Nemeyer |
| 2,650,588 | A | 9/1953 | Drew |
| 2,697,433 | A | 12/1954 | Sehnder |

(Continued)

FOREIGN PATENT DOCUMENTS

CA 964149 3/1975

(Continued)

OTHER PUBLICATIONS

"Prestige Cervical Disc System Surgical Technique", 12 pgs.

(Continued)

*Primary Examiner* — Victor Nguyen
(74) *Attorney, Agent, or Firm* — Harness Dickey

(57) ABSTRACT

A guide is disclosed for use in performing spinal surgery to prepare across a spinal disc and adjacent vertebrae an implantation space. The guide is associated with a computer controlled surgical navigation system employing an energy-detecting array to track positions of the guide in three dimensional space relative to a known reference point. The guide includes a body for providing protected access to prepare across the spinal disc and into the adjacent vertebrae the implantation space. The body has a passage adapted to receive a bone removal device for forming the implantation space through the body. At least one electrically energizable energy emitter array is attached to the body for use in identifying the location of the guide relative to the adjacent vertebrae. A system and method for using the guide in spinal surgery are also disclosed.

14 Claims, 10 Drawing Sheets

U.S. PATENT DOCUMENTS

| | | |
|---|---|---|
| 3,016,899 A | 1/1962 | Stenvall |
| 3,017,887 A | 1/1962 | Heyer |
| 3,061,936 A | 11/1962 | Dobbeleer |
| 3,073,310 A | 1/1963 | Mocarski |
| 3,109,588 A | 11/1963 | Polhemus et al. |
| 3,294,083 A | 12/1966 | Alderson |
| 3,367,326 A | 2/1968 | Frazier |
| 3,439,256 A | 4/1969 | Kahne |
| 3,577,160 A | 5/1971 | White |
| 3,614,950 A | 10/1971 | Rabey |
| 3,644,825 A | 2/1972 | Davis, Jr. et al. |
| 3,674,014 A | 7/1972 | Tillander |
| 3,702,935 A | 11/1972 | Carey et al. |
| 3,704,707 A | 12/1972 | Halloran |
| 3,821,469 A | 6/1974 | Whetstone et al. |
| 3,868,565 A | 2/1975 | Kuipers |
| 3,941,127 A | 3/1976 | Froning |
| 3,983,474 A | 9/1976 | Kuipers |
| 4,017,858 A | 4/1977 | Kuipers |
| 4,037,592 A | 7/1977 | Kronner |
| 4,052,620 A | 10/1977 | Brunnett |
| 4,054,881 A | 10/1977 | Raab |
| 4,117,337 A | 9/1978 | Staats |
| 4,173,228 A | 11/1979 | Van Steenwyk et al. |
| 4,182,312 A | 1/1980 | Mushabac |
| 4,202,349 A | 5/1980 | Jones |
| 4,228,799 A | 10/1980 | Anichkov et al. |
| 4,256,112 A | 3/1981 | Kopf et al. |
| 4,262,306 A | 4/1981 | Renner |
| 4,287,809 A | 9/1981 | Egli et al. |
| 4,298,874 A | 11/1981 | Kuipers |
| 4,314,251 A | 2/1982 | Raab |
| 4,317,078 A | 2/1982 | Weed et al. |
| 4,319,136 A | 3/1982 | Jinkins |
| 4,328,548 A | 5/1982 | Crow et al. |
| 4,328,813 A | 5/1982 | Ray |
| 4,339,953 A | 7/1982 | Iwasaki |
| 4,341,220 A | 7/1982 | Perry |
| 4,346,384 A | 8/1982 | Raab |
| 4,358,856 A | 11/1982 | Stivender et al. |
| 4,368,536 A | 1/1983 | Pfeiler |
| 4,368,556 A | 1/1983 | Wanner et al. |
| 4,396,885 A | 8/1983 | Constant |
| 4,396,945 A | 8/1983 | DiMatteo et al. |
| 4,403,321 A | 9/1983 | Kruger |
| 4,418,422 A | 11/1983 | Richter et al. |
| 4,419,012 A | 12/1983 | Stephenson et al. |
| 4,422,041 A | 12/1983 | Lienau |
| 4,431,005 A | 2/1984 | McCormick |
| 4,485,815 A | 12/1984 | Amplatz et al. |
| 4,506,676 A | 3/1985 | Duska |
| 4,543,959 A | 10/1985 | Sepponen |
| 4,548,208 A | 10/1985 | Niemi |
| 4,571,834 A | 2/1986 | Fraser et al. |
| 4,572,198 A | 2/1986 | Codrington |
| 4,583,538 A | 4/1986 | Onik et al. |
| 4,584,577 A | 4/1986 | Temple |
| 4,608,977 A | 9/1986 | Brown |
| 4,613,866 A | 9/1986 | Blood |
| 4,617,925 A | 10/1986 | Laitinen |
| 4,618,978 A | 10/1986 | Cosman |
| 4,621,628 A | 11/1986 | Brudermann |
| 4,625,718 A | 12/1986 | Olerud et al. |
| 4,638,798 A | 1/1987 | Shelden et al. |
| 4,642,786 A | 2/1987 | Hansen |
| 4,645,343 A | 2/1987 | Stockdale et al. |
| 4,649,504 A | 3/1987 | Krouglicof et al. |
| 4,651,732 A | 3/1987 | Frederick |
| 4,653,509 A | 3/1987 | Oloff et al. |
| 4,659,971 A | 4/1987 | Suzuki et al. |
| 4,660,970 A | 4/1987 | Ferrano |
| 4,673,352 A | 6/1987 | Hansen |
| 4,688,037 A | 8/1987 | Krieg |
| 4,701,049 A | 10/1987 | Beckman et al. |
| 4,705,395 A | 11/1987 | Hageniers |
| 4,705,401 A | 11/1987 | Addleman et al. |
| 4,706,665 A | 11/1987 | Gouda |
| 4,709,156 A | 11/1987 | Murphy et al. |
| 4,710,708 A | 12/1987 | Rorden et al. |
| 4,719,419 A | 1/1988 | Dawley |
| 4,722,056 A | 1/1988 | Roberts et al. |
| 4,722,336 A | 2/1988 | Kim et al. |
| 4,723,544 A | 2/1988 | Moore et al. |
| 4,727,565 A | 2/1988 | Ericson |
| RE32,619 E | 3/1988 | Damadian |
| 4,733,969 A | 3/1988 | Case et al. |
| 4,736,738 A * | 4/1988 | Lipovsek et al. ............... 606/88 |
| 4,737,032 A | 4/1988 | Addleman et al. |
| 4,737,794 A | 4/1988 | Jones |
| 4,737,921 A | 4/1988 | Goldwasser et al. |
| 4,742,356 A | 5/1988 | Kuipers |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,528 A | 6/1988 | Hines et al. |
| 4,761,072 A | 8/1988 | Pryor |
| 4,764,016 A | 8/1988 | Johansson |
| 4,771,787 A | 9/1988 | Wurster et al. |
| 4,779,212 A | 10/1988 | Levy |
| 4,782,239 A | 11/1988 | Hirose et al. |
| 4,788,481 A | 11/1988 | Niwa |
| 4,791,934 A | 12/1988 | Brunnett |
| 4,793,355 A | 12/1988 | Crum et al. |
| 4,794,262 A | 12/1988 | Sato et al. |
| 4,797,907 A | 1/1989 | Anderton |
| 4,803,976 A | 2/1989 | Frigg et al. |
| 4,804,261 A | 2/1989 | Kirschen |
| 4,805,615 A | 2/1989 | Carol |
| 4,809,694 A | 3/1989 | Ferrara |
| 4,821,200 A | 4/1989 | Oberg |
| 4,821,206 A | 4/1989 | Arora |
| 4,821,731 A | 4/1989 | Martinelli et al. |
| 4,822,163 A | 4/1989 | Schmidt |
| 4,825,091 A | 4/1989 | Breyer et al. |
| 4,829,373 A | 5/1989 | Leberl et al. |
| 4,836,778 A | 6/1989 | Baumrind et al. |
| 4,838,265 A | 6/1989 | Cosman et al. |
| 4,841,967 A | 6/1989 | Chang et al. |
| 4,845,771 A | 7/1989 | Wislocki et al. |
| 4,849,692 A | 7/1989 | Blood |
| 4,860,331 A | 8/1989 | Williams et al. |
| 4,862,893 A | 9/1989 | Martinelli |
| 4,869,247 A | 9/1989 | Howard, III et al. |
| 4,875,165 A | 10/1989 | Fencil et al. |
| 4,875,478 A | 10/1989 | Chen |
| 4,884,566 A | 12/1989 | Mountz et al. |
| 4,889,526 A | 12/1989 | Rauscher et al. |
| 4,896,673 A | 1/1990 | Rose et al. |
| 4,905,698 A | 3/1990 | Strohl, Jr. et al. |
| 4,923,459 A | 5/1990 | Nambu |
| 4,931,056 A | 6/1990 | Ghajar et al. |
| 4,945,305 A | 7/1990 | Blood |
| 4,945,914 A | 8/1990 | Allen |
| 4,951,653 A | 8/1990 | Fry et al. |
| 4,955,891 A | 9/1990 | Carol |
| 4,961,422 A | 10/1990 | Marchosky et al. |
| 4,977,655 A | 12/1990 | Martinelli |
| 4,989,608 A | 2/1991 | Ratner |
| 4,991,579 A | 2/1991 | Allen |
| 5,002,058 A | 3/1991 | Martinelli |
| 5,005,592 A | 4/1991 | Cartmell |
| 5,013,317 A | 5/1991 | Cole et al. |
| 5,015,247 A | 5/1991 | Michelson |
| 5,016,639 A | 5/1991 | Allen |
| 5,017,139 A | 5/1991 | Mushabac |
| 5,027,818 A | 7/1991 | Bova et al. |
| 5,030,196 A | 7/1991 | Inoue |
| 5,030,222 A | 7/1991 | Calandruccio et al. |
| 5,031,203 A | 7/1991 | Trecha |
| 5,042,486 A | 8/1991 | Pfeiler et al. |
| 5,047,036 A | 9/1991 | Koutrouvelis |
| 5,050,608 A | 9/1991 | Watanabe et al. |
| 5,054,492 A | 10/1991 | Scribner et al. |
| 5,057,095 A | 10/1991 | Fabian |
| 5,059,789 A | 10/1991 | Salcudean |

| Patent | Date | Inventor |
|---|---|---|
| 5,078,140 A | 1/1992 | Kwoh |
| 5,079,699 A | 1/1992 | Tuy et al. |
| 5,086,401 A | 2/1992 | Glassman et al. |
| 5,094,241 A | 3/1992 | Allen |
| 5,097,839 A | 3/1992 | Allen |
| 5,098,426 A | 3/1992 | Sklar et al. |
| 5,099,845 A | 3/1992 | Besz et al. |
| 5,099,846 A | 3/1992 | Hardy |
| 5,105,829 A | 4/1992 | Fabian et al. |
| 5,107,839 A | 4/1992 | Houdek et al. |
| 5,107,843 A | 4/1992 | Aarnio et al. |
| 5,107,862 A | 4/1992 | Fabian et al. |
| 5,109,194 A | 4/1992 | Cantaloube |
| 5,119,817 A | 6/1992 | Allen |
| 5,142,930 A | 9/1992 | Allen et al. |
| 5,143,076 A | 9/1992 | Hardy et al. |
| 5,152,288 A | 10/1992 | Hoenig et al. |
| 5,160,337 A | 11/1992 | Cosman |
| 5,161,536 A | 11/1992 | Vilkomerson et al. |
| 5,178,164 A | 1/1993 | Allen |
| 5,178,621 A | 1/1993 | Cook et al. |
| 5,186,174 A | 2/1993 | Schlondorff et al. |
| 5,187,475 A | 2/1993 | Wagener et al. |
| 5,188,126 A | 2/1993 | Fabian et al. |
| 5,190,059 A | 3/1993 | Fabian et al. |
| 5,193,106 A | 3/1993 | DeSena |
| 5,197,476 A | 3/1993 | Nowacki et al. |
| 5,197,965 A | 3/1993 | Cherry et al. |
| 5,198,768 A | 3/1993 | Keren |
| 5,198,877 A | 3/1993 | Schulz |
| 5,207,688 A | 5/1993 | Carol |
| 5,211,164 A | 5/1993 | Allen |
| 5,211,165 A | 5/1993 | Dumoulin et al. |
| 5,211,176 A | 5/1993 | Ishiguro et al. |
| 5,212,720 A | 5/1993 | Landi et al. |
| 5,214,615 A | 5/1993 | Bauer |
| 5,219,351 A | 6/1993 | Teubner et al. |
| 5,222,499 A | 6/1993 | Allen et al. |
| 5,224,049 A | 6/1993 | Mushabac |
| 5,228,442 A | 7/1993 | Imran |
| 5,230,338 A | 7/1993 | Allen et al. |
| 5,230,623 A | 7/1993 | Guthrie et al. |
| 5,233,990 A | 8/1993 | Barnea |
| 5,237,996 A | 8/1993 | Waldman et al. |
| 5,249,581 A | 10/1993 | Horbal et al. |
| 5,251,127 A | 10/1993 | Raab |
| 5,251,635 A | 10/1993 | Dumoulin et al. |
| 5,253,647 A | 10/1993 | Takahashi et al. |
| 5,255,680 A | 10/1993 | Darrow et al. |
| 5,257,636 A | 11/1993 | White |
| 5,257,998 A | 11/1993 | Ota et al. |
| 5,261,404 A | 11/1993 | Mick et al. |
| 5,265,610 A | 11/1993 | Darrow et al. |
| 5,265,611 A | 11/1993 | Hoenig et al. |
| 5,269,759 A | 12/1993 | Hernandez et al. |
| 5,271,400 A | 12/1993 | Dumoulin et al. |
| 5,273,025 A | 12/1993 | Sakiyama et al. |
| 5,274,551 A | 12/1993 | Corby, Jr. |
| 5,279,309 A | 1/1994 | Taylor et al. |
| 5,285,787 A | 2/1994 | Machida |
| 5,291,199 A | 3/1994 | Overman et al. |
| 5,291,889 A | 3/1994 | Kenet et al. |
| 5,295,483 A | 3/1994 | Nowacki et al. |
| 5,297,549 A | 3/1994 | Beatty et al. |
| 5,299,253 A | 3/1994 | Wessels |
| 5,299,254 A | 3/1994 | Dancer et al. |
| 5,299,288 A | 3/1994 | Glassman et al. |
| 5,300,080 A | 4/1994 | Clayman et al. |
| 5,305,091 A | 4/1994 | Gelbart et al. |
| 5,305,203 A | 4/1994 | Raab |
| 5,306,271 A | 4/1994 | Zinreich et al. |
| 5,307,072 A | 4/1994 | Jones, Jr. |
| 5,309,913 A | 5/1994 | Kormos et al. |
| 5,315,630 A | 5/1994 | Sturm et al. |
| 5,316,024 A | 5/1994 | Hirschi et al. |
| 5,318,025 A | 6/1994 | Dumoulin et al. |
| 5,320,111 A | 6/1994 | Livingston |
| 5,325,728 A | 7/1994 | Zimmerman et al. |
| 5,325,873 A | 7/1994 | Hirschi et al. |
| 5,329,944 A | 7/1994 | Fabian et al. |
| 5,330,485 A | 7/1994 | Clayman et al. |
| 5,333,168 A | 7/1994 | Fernandes et al. |
| 5,353,795 A | 10/1994 | Souza et al. |
| 5,353,800 A | 10/1994 | Pohndorf et al. |
| 5,353,807 A | 10/1994 | DeMarco |
| 5,359,417 A | 10/1994 | Muller et al. |
| 5,368,030 A | 11/1994 | Zinreich et al. |
| 5,371,778 A | 12/1994 | Yanof et al. |
| 5,375,596 A | 12/1994 | Twiss et al. |
| 5,377,678 A | 1/1995 | Dumoulin et al. |
| 5,383,454 A * | 1/1995 | Bucholz ........................ 600/429 |
| 5,385,146 A | 1/1995 | Goldreyer |
| 5,385,148 A | 1/1995 | Lesh et al. |
| 5,386,828 A | 2/1995 | Owens et al. |
| 5,389,101 A | 2/1995 | Heilbrun et al. |
| 5,391,199 A | 2/1995 | Ben-Haim |
| 5,394,457 A | 2/1995 | Leibinger et al. |
| 5,394,875 A | 3/1995 | Lewis et al. |
| 5,397,329 A | 3/1995 | Allen |
| 5,398,684 A | 3/1995 | Hardy |
| 5,399,146 A | 3/1995 | Nowacki et al. |
| 5,400,384 A | 3/1995 | Fernandes et al. |
| 5,402,801 A | 4/1995 | Taylor |
| 5,408,409 A | 4/1995 | Glassman et al. |
| 5,413,573 A | 5/1995 | Koivukangas |
| 5,417,210 A | 5/1995 | Funda et al. |
| 5,419,325 A | 5/1995 | Dumoulin et al. |
| 5,423,334 A | 6/1995 | Jordan |
| 5,425,367 A | 6/1995 | Shapiro et al. |
| 5,425,382 A | 6/1995 | Golden et al. |
| 5,426,683 A | 6/1995 | O'Farrell, Jr. et al. |
| 5,426,687 A | 6/1995 | Goodall et al. |
| 5,427,097 A | 6/1995 | Depp |
| 5,429,132 A | 7/1995 | Guy et al. |
| 5,433,198 A | 7/1995 | Desai |
| RE35,025 E | 8/1995 | Anderton |
| 5,437,277 A * | 8/1995 | Dumoulin et al. ............. 600/424 |
| 5,443,066 A | 8/1995 | Dumoulin et al. |
| 5,443,489 A | 8/1995 | Ben-Haim |
| 5,444,756 A | 8/1995 | Pai et al. |
| 5,445,144 A | 8/1995 | Wodicka et al. |
| 5,445,150 A | 8/1995 | Dumoulin et al. |
| 5,445,166 A | 8/1995 | Taylor |
| 5,446,548 A | 8/1995 | Gerig et al. |
| 5,447,154 A | 9/1995 | Cinquin et al. |
| 5,448,610 A | 9/1995 | Yamamoto et al. |
| 5,453,686 A | 9/1995 | Anderson |
| 5,456,718 A | 10/1995 | Szymaitis |
| 5,457,641 A | 10/1995 | Zimmer et al. |
| 5,458,718 A | 10/1995 | Venkitachalam |
| 5,464,446 A | 11/1995 | Dreessen et al. |
| 5,469,847 A | 11/1995 | Zinreich et al. |
| 5,478,341 A | 12/1995 | Cook et al. |
| 5,478,343 A | 12/1995 | Ritter |
| 5,480,422 A | 1/1996 | Ben-Haim |
| 5,480,439 A | 1/1996 | Bisek et al. |
| 5,483,961 A | 1/1996 | Kelly et al. |
| 5,484,437 A | 1/1996 | Michelson |
| 5,485,849 A | 1/1996 | Panescu et al. |
| 5,487,391 A | 1/1996 | Panescu |
| 5,487,729 A | 1/1996 | Avellanet et al. |
| 5,487,757 A | 1/1996 | Truckai et al. |
| 5,490,196 A | 2/1996 | Rudich et al. |
| 5,494,034 A | 2/1996 | Schlondorff et al. |
| 5,503,416 A | 4/1996 | Aoki et al. |
| 5,513,637 A | 5/1996 | Twiss et al. |
| 5,514,146 A | 5/1996 | Lam et al. |
| 5,515,160 A | 5/1996 | Schulz et al. |
| 5,517,990 A | 5/1996 | Kalfas et al. |
| 5,526,812 A | 6/1996 | Dumoulin et al. |
| 5,531,227 A | 7/1996 | Schneider |
| 5,531,520 A | 7/1996 | Grimson et al. |
| 5,534,005 A * | 7/1996 | Tokish et al. ................... 606/80 |
| 5,542,938 A | 8/1996 | Avellanet et al. |
| 5,543,951 A | 8/1996 | Moehrmann |
| 5,546,940 A | 8/1996 | Panescu et al. |
| 5,546,949 A | 8/1996 | Frazin et al. |
| 5,546,951 A | 8/1996 | Ben-Haim |

| | | | | | |
|---|---|---|---|---|---|
| 5,551,429 A | 9/1996 | Fitzpatrick et al. | 5,769,861 A | 6/1998 | Vilsmeier |
| 5,558,091 A | 9/1996 | Acker et al. | 5,772,594 A | 6/1998 | Barrick |
| 5,566,681 A | 10/1996 | Manwaring et al. | 5,772,661 A | 6/1998 | Michelson |
| 5,568,384 A | 10/1996 | Robb et al. | 5,775,322 A | 7/1998 | Silverstein et al. |
| 5,568,809 A | 10/1996 | Ben-haim | 5,776,064 A | 7/1998 | Kalfas et al. |
| 5,571,109 A | 11/1996 | Bertagnoli et al. | 5,782,765 A | 7/1998 | Jonkman |
| 5,572,999 A | 11/1996 | Funda et al. | 5,787,886 A | 8/1998 | Kelly et al. |
| 5,573,533 A | 11/1996 | Strul | 5,792,055 A | 8/1998 | McKinnon |
| 5,575,794 A | 11/1996 | Walus et al. | 5,795,294 A | 8/1998 | Luber et al. |
| 5,575,798 A | 11/1996 | Koutrouvelis | 5,797,849 A | 8/1998 | Vesely et al. |
| 5,583,909 A | 12/1996 | Hanover | 5,799,055 A | 8/1998 | Peshkin et al. |
| 5,588,430 A | 12/1996 | Bova et al. | 5,799,099 A | 8/1998 | Wang et al. |
| 5,590,215 A | 12/1996 | Allen | 5,800,352 A | 9/1998 | Ferre et al. |
| 5,592,939 A | 1/1997 | Martinelli | 5,800,535 A | 9/1998 | Howard, III |
| 5,593,409 A | 1/1997 | Michelson | 5,802,719 A | 9/1998 | O'Farrell, Jr. et al. |
| 5,595,193 A | 1/1997 | Walus et al. | 5,803,089 A | 9/1998 | Ferre et al. |
| 5,596,228 A | 1/1997 | Anderton et al. | 5,807,252 A | 9/1998 | Hassfeld et al. |
| 5,600,330 A | 2/1997 | Blood | 5,810,008 A | 9/1998 | Dekel et al. |
| 5,603,318 A | 2/1997 | Heilbrun et al. | 5,810,728 A | 9/1998 | Kuhn |
| 5,611,025 A | 3/1997 | Lorensen et al. | 5,810,735 A | 9/1998 | Halperin et al. |
| 5,617,462 A | 4/1997 | Spratt | 5,820,553 A | 10/1998 | Hughes |
| 5,617,857 A | 4/1997 | Chader et al. | 5,823,192 A | 10/1998 | Kalend et al. |
| 5,619,261 A | 4/1997 | Anderton | 5,823,958 A | 10/1998 | Truppe |
| 5,622,169 A | 4/1997 | Golden et al. | 5,828,725 A | 10/1998 | Levinson |
| 5,622,170 A | 4/1997 | Schulz | 5,828,770 A | 10/1998 | Leis et al. |
| 5,627,873 A | 5/1997 | Hanover et al. | 5,829,444 A | 11/1998 | Ferre et al. |
| 5,628,315 A | 5/1997 | Vilsmeier et al. | 5,831,260 A | 11/1998 | Hansen |
| 5,630,431 A | 5/1997 | Taylor | 5,833,608 A | 11/1998 | Acker |
| 5,636,644 A | 6/1997 | Hart et al. | 5,834,759 A | 11/1998 | Glossop |
| 5,638,819 A | 6/1997 | Manwaring et al. | 5,836,954 A | 11/1998 | Heilbrun et al. |
| 5,640,170 A | 6/1997 | Anderson | 5,840,024 A | 11/1998 | Taniguchi et al. |
| 5,642,395 A | 6/1997 | Anderton et al. | 5,840,025 A | 11/1998 | Ben-Haim |
| 5,643,268 A | 7/1997 | Vilsmeier et al. | 5,843,076 A | 12/1998 | Webster, Jr. et al. |
| 5,645,065 A | 7/1997 | Shapiro et al. | 5,848,967 A | 12/1998 | Cosman |
| 5,646,524 A | 7/1997 | Gilboa | 5,851,183 A | 12/1998 | Bucholz |
| 5,647,361 A | 7/1997 | Damadian | 5,865,846 A | 2/1999 | Bryan et al. |
| 5,662,111 A | 9/1997 | Cosman | 5,868,674 A | 2/1999 | Glowinski et al. |
| 5,664,001 A | 9/1997 | Tachibana et al. | 5,868,675 A | 2/1999 | Henrion et al. |
| 5,674,296 A | 10/1997 | Bryan et al. | 5,871,445 A | 2/1999 | Bucholz |
| 5,676,673 A * | 10/1997 | Ferre et al. ............ 606/130 | 5,871,455 A | 2/1999 | Ueno |
| 5,681,260 A | 10/1997 | Ueda et al. | 5,871,487 A | 2/1999 | Warner et al. |
| 5,682,886 A | 11/1997 | Delp et al. | 5,873,822 A | 2/1999 | Ferre et al. |
| 5,682,890 A | 11/1997 | Kormos et al. | 5,882,304 A | 3/1999 | Ehnholm et al. |
| 5,690,108 A | 11/1997 | Chakeres | 5,884,410 A | 3/1999 | Prinz |
| 5,694,945 A | 12/1997 | Ben-Haim | 5,889,834 A | 3/1999 | Vilsmeier et al. |
| 5,695,500 A | 12/1997 | Taylor et al. | 5,891,034 A | 4/1999 | Bucholz |
| 5,695,501 A | 12/1997 | Carol et al. | 5,891,157 A | 4/1999 | Day et al. |
| 5,697,377 A | 12/1997 | Wittkampf | 5,904,691 A | 5/1999 | Barnett et al. |
| 5,702,406 A | 12/1997 | Vilsmeier et al. | 5,907,395 A | 5/1999 | Schulz et al. |
| 5,711,299 A | 1/1998 | Manwaring et al. | 5,913,820 A | 6/1999 | Bladen et al. |
| 5,713,946 A | 2/1998 | Ben-Haim | 5,920,395 A | 7/1999 | Schulz |
| 5,715,822 A | 2/1998 | Watkins et al. | 5,921,992 A | 7/1999 | Costales et al. |
| 5,715,836 A | 2/1998 | Kliegis et al. | 5,923,727 A | 7/1999 | Navab |
| 5,718,241 A | 2/1998 | Ben-Haim et al. | 5,928,248 A | 7/1999 | Acker |
| 5,727,552 A | 3/1998 | Ryan | 5,938,603 A | 8/1999 | Ponzi |
| 5,727,553 A | 3/1998 | Saad | 5,938,694 A | 8/1999 | Jaraczewski et al. |
| 5,729,129 A | 3/1998 | Acker | 5,947,980 A | 9/1999 | Jensen et al. |
| 5,730,129 A | 3/1998 | Darrow et al. | 5,947,981 A | 9/1999 | Cosman |
| 5,730,130 A | 3/1998 | Fitzpatrick et al. | 5,950,629 A | 9/1999 | Taylor et al. |
| 5,732,703 A | 3/1998 | Kalfas et al. | 5,951,475 A | 9/1999 | Gueziec et al. |
| 5,735,278 A | 4/1998 | Hoult et al. | 5,951,571 A | 9/1999 | Audette |
| 5,738,096 A | 4/1998 | Ben-Haim | 5,954,647 A | 9/1999 | Bova et al. |
| 5,740,802 A | 4/1998 | Nafis et al. | 5,957,844 A | 9/1999 | Dekel et al. |
| 5,741,214 A | 4/1998 | Ouchi et al. | 5,964,796 A | 10/1999 | Imran |
| 5,742,394 A | 4/1998 | Hansen | 5,967,980 A | 10/1999 | Ferre et al. |
| 5,744,953 A | 4/1998 | Hansen | 5,967,982 A | 10/1999 | Barnett |
| 5,748,767 A | 5/1998 | Raab | 5,968,047 A | 10/1999 | Reed |
| 5,749,362 A | 5/1998 | Funda et al. | 5,971,997 A | 10/1999 | Guthrie et al. |
| 5,749,835 A | 5/1998 | Glantz | 5,976,156 A | 11/1999 | Taylor et al. |
| 5,752,513 A | 5/1998 | Acker et al. | 5,980,535 A | 11/1999 | Barnett et al. |
| 5,755,725 A | 5/1998 | Druais | 5,983,126 A | 11/1999 | Wittkampf |
| RE35,816 E | 6/1998 | Schulz | 5,987,349 A | 11/1999 | Schulz |
| 5,758,667 A | 6/1998 | Slettenmark | 5,987,960 A | 11/1999 | Messner et al. |
| 5,762,064 A | 6/1998 | Polvani | 5,999,837 A | 12/1999 | Messner et al. |
| 5,767,669 A | 6/1998 | Hansen et al. | 5,999,840 A | 12/1999 | Grimson et al. |
| 5,767,699 A | 6/1998 | Bosnyak et al. | 6,001,130 A | 12/1999 | Bryan et al. |
| 5,767,960 A | 6/1998 | Orman | 6,006,126 A | 12/1999 | Cosman |
| 5,769,789 A | 6/1998 | Wang et al. | 6,006,127 A | 12/1999 | Van Der Brug et al. |
| 5,769,843 A | 6/1998 | Abela et al. | 6,013,087 A | 1/2000 | Adams et al. |

| | | | |
|---|---|---|---|
| 6,014,580 A | 1/2000 | Blume et al. | |
| 6,016,439 A | 1/2000 | Acker | |
| 6,019,725 A | 2/2000 | Vesely et al. | |
| 6,021,343 A * | 2/2000 | Foley et al. ............... 600/429 | |
| 6,024,695 A | 2/2000 | Taylor et al. | |
| 6,050,724 A | 4/2000 | Schmitz et al. | |
| 6,059,718 A | 5/2000 | Taniguchi et al. | |
| 6,063,022 A | 5/2000 | Ben-Haim | |
| 6,071,288 A | 6/2000 | Carol et al. | |
| 6,073,043 A | 6/2000 | Schneider | |
| 6,076,008 A | 6/2000 | Bucholz | |
| 6,096,050 A | 8/2000 | Audette | |
| 6,104,944 A | 8/2000 | Martinelli | |
| 6,118,845 A | 9/2000 | Simon et al. | |
| 6,122,538 A | 9/2000 | Sliwa, Jr. et al. | |
| 6,122,541 A | 9/2000 | Cosman et al. | |
| 6,131,396 A | 10/2000 | Duerr et al. | |
| 6,139,183 A | 10/2000 | Graumann | |
| 6,147,480 A | 11/2000 | Osadchy et al. | |
| 6,149,592 A | 11/2000 | Yanof et al. | |
| 6,156,067 A | 12/2000 | Bryan et al. | |
| 6,161,032 A | 12/2000 | Acker | |
| 6,165,181 A | 12/2000 | Heilbrun et al. | |
| 6,167,296 A | 12/2000 | Shahidi | |
| 6,172,499 B1 | 1/2001 | Ashe | |
| 6,175,756 B1 | 1/2001 | Ferre et al. | |
| 6,178,345 B1 | 1/2001 | Vilsmeier et al. | |
| 6,194,639 B1 | 2/2001 | Botella et al. | |
| 6,201,387 B1 | 3/2001 | Govari | |
| 6,203,497 B1 | 3/2001 | Dekel et al. | |
| 6,211,666 B1 | 4/2001 | Acker | |
| 6,223,067 B1 | 4/2001 | Vilsmeier et al. | |
| 6,233,476 B1 | 5/2001 | Strommer et al. | |
| 6,246,231 B1 | 6/2001 | Ashe | |
| 6,259,942 B1 | 7/2001 | Westermann et al. | |
| 6,273,896 B1 | 8/2001 | Franck et al. | |
| 6,285,902 B1 | 9/2001 | Kienzle, III et al. | |
| 6,298,262 B1 | 10/2001 | Franck et al. | |
| 6,314,310 B1 | 11/2001 | Ben-Haim et al. | |
| 6,332,089 B1 | 12/2001 | Acker et al. | |
| 6,341,231 B1 | 1/2002 | Ferre et al. | |
| 6,348,058 B1 * | 2/2002 | Melkent et al. ............... 606/130 | |
| 6,351,659 B1 | 2/2002 | Vilsmeier | |
| 6,381,485 B1 | 4/2002 | Hunter et al. | |
| 6,424,856 B1 | 7/2002 | Vilsmeier et al. | |
| 6,427,314 B1 | 8/2002 | Acker | |
| 6,428,547 B1 | 8/2002 | Vilsmeier et al. | |
| 6,434,415 B1 | 8/2002 | Foley et al. | |
| 6,437,567 B1 | 8/2002 | Schenck et al. | |
| 6,445,943 B1 | 9/2002 | Ferre et al. | |
| 6,470,207 B1 | 10/2002 | Simon et al. | |
| 6,474,341 B1 | 11/2002 | Hunter et al. | |
| 6,478,802 B2 | 11/2002 | Kienzle, III et al. | |
| 6,484,049 B1 | 11/2002 | Seeley et al. | |
| 6,490,475 B1 | 12/2002 | Seeley et al. | |
| 6,493,573 B1 | 12/2002 | Martinelli et al. | |
| 6,498,944 B1 | 12/2002 | Ben-Haim et al. | |
| 6,499,488 B1 | 12/2002 | Hunter et al. | |
| 6,516,046 B1 | 2/2003 | Frohlich et al. | |
| 6,527,443 B1 | 3/2003 | Vilsmeier et al. | |
| 6,551,325 B2 | 4/2003 | Neubauer et al. | |
| 6,584,174 B2 | 6/2003 | Schubert et al. | |
| 6,609,022 B2 | 8/2003 | Vilsmeier et al. | |
| 6,611,700 B1 | 8/2003 | Vilsmeier et al. | |
| 6,640,128 B2 | 10/2003 | Vilsmeier et al. | |
| 6,694,162 B2 | 2/2004 | Hartlep | |
| 6,701,179 B1 | 3/2004 | Martinelli et al. | |
| 6,796,988 B2 | 9/2004 | Melkent et al. | |
| 2001/0007918 A1 | 7/2001 | Vilsmeier et al. | |
| 2002/0095081 A1 | 7/2002 | Vilsmeier et al. | |
| 2002/0151894 A1 | 10/2002 | Melkent et al. | |
| 2004/0024309 A1 | 2/2004 | Ferre et al. | |
| 2005/0059885 A1 | 3/2005 | Melkent et al. | |

FOREIGN PATENT DOCUMENTS

| | | | |
|---|---|---|---|
| DE | 3042343 | 6/1982 | |
| DE | 3508730 | 9/1986 | |
| DE | 3717871 | 12/1988 | |
| DE | 3831278 A1 | 3/1989 | |
| DE | 3838011 | 7/1989 | |
| DE | 4213426 A1 | 10/1992 | |
| DE | 4225112 | 12/1993 | |
| DE | 4233978 | 4/1994 | |
| DE | 19715202 | 10/1998 | |
| DE | 19751761 | 10/1998 | |
| DE | 19832296 | 2/1999 | |
| DE | 19747427 | 5/1999 | |
| DE | 10085137 | 11/2002 | |
| EP | 0062941 | 10/1982 | |
| EP | 0119660 | 9/1984 | |
| EP | 0155857 | 9/1985 | |
| EP | 0319844 | 6/1989 | |
| EP | 0326768 | 8/1989 | |
| EP | 350996 A1 | 1/1990 | |
| EP | 0419729 A1 | 4/1991 | |
| EP | 0427358 | 5/1991 | |
| EP | 0456103 | 11/1991 | |
| EP | 0469966 A1 | 2/1992 | |
| EP | 0581704 | 2/1994 | |
| EP | 0651968 | 5/1995 | |
| EP | 0655138 | 5/1995 | |
| EP | 0676178 A1 | 10/1995 | |
| EP | 0894473 A2 | 2/1999 | |
| EP | 0908146 | 4/1999 | |
| EP | 0930046 | 7/1999 | |
| FR | 2417970 | 9/1979 | |
| FR | 2618211 A1 | 1/1989 | |
| GB | 2094590 A | 9/1982 | |
| GB | 2164856 A | 4/1986 | |
| JP | 62327 | 1/1983 | |
| JP | 2765738 | 6/1988 | |
| JP | 63240851 | 10/1988 | |
| JP | 3267054 | 11/1991 | |
| JP | 6194639 | 7/1994 | |
| JP | 07008514 A | 1/1995 | |
| WO | WO-8809151 | 12/1988 | |
| WO | WO-8905123 | 6/1989 | |
| WO | WO-9005494 A1 | 5/1990 | |
| WO | WO-9103982 A1 | 4/1991 | |
| WO | WO-9104711 | 4/1991 | |
| WO | WO-9107726 | 5/1991 | |
| WO | WO-9203090 | 3/1992 | |
| WO | WO-9206645 | 4/1992 | |
| WO | WO-9404938 | 3/1994 | |
| WO | WO-9423647 | 10/1994 | |
| WO | WO-9424933 A1 | 11/1994 | |
| WO | WO-9428824 A2 | 12/1994 | |
| WO | WO-9507055 A1 | 3/1995 | |
| WO | WO 96/11624 * | 4/1996 | .............. 606/130 |
| WO | WO-9611624 | 4/1996 | |
| WO | WO-9632059 A1 | 10/1996 | |
| WO | WO-9730666 A2 | 8/1997 | |
| WO | WO-9736192 A1 | 10/1997 | |
| WO | WO-9740764 A2 | 11/1997 | |
| WO | WO-9749453 A1 | 12/1997 | |
| WO | WO-9808554 A1 | 3/1998 | |
| WO | WO-9838908 | 9/1998 | |
| WO | WO-9915097 A2 | 4/1999 | |
| WO | WO-9921498 A1 | 5/1999 | |
| WO | WO-9923956 A1 | 5/1999 | |
| WO | WO-9926549 A1 | 6/1999 | |
| WO | WO-9927839 A2 | 6/1999 | |
| WO | WO-9929253 A1 | 6/1999 | |
| WO | WO-9933406 A1 | 7/1999 | |
| WO | WO-9937208 A1 | 7/1999 | |
| WO | WO-9938449 A1 | 8/1999 | |
| WO | WO-9952094 A1 | 10/1999 | |
| WO | WO-9960939 A1 | 12/1999 | |
| WO | WO-0130437 A1 | 5/2001 | |

OTHER PUBLICATIONS

Adams et al., "Orientation Aid for Head and Neck Surgeons," Innov. Tech. Biol. Med., vol. 13, No. 4, 1992, pp. 409-424.

Adams et al., Computer-Assisted Surgery, IEEE Computer Graphics & Applications, pp. 43-51, (May 1990).

Barrick et al., "Prophylactic Intramedullary Fixation of the Tibia for Stress Fracture in a Professional Athlete," Journal of Orthopaedic Trauma, vol. 6, No. 2, pp. 241-244 (1992).

Barrick et al., "Technical Difficulties with the Brooker-Wills Nail in Acute Fractures of the Femur," Journal of Orthopaedic Trauma, vol. 4, No. 2, pp. 144-150 (1990).

Barrick, "Distal Locking Screw Insertion Using a Cannulated Drill Bit: Technical Note," Journal of Orthopaedic Trauma, vol. 7, No. 3, 1993, pp. 248-251.

Batnitzky et al., "Three-Dimensinal Computer Reconstructions of Brain Lesions from Surface Contours Provided by Computed Tomography: A Prospectus," Neurosurgery, vol. 11, No. 1, Part 1, 1982, pp. 73-84.

Benzel et al., "Magnetic Source Imaging: a Review of the Magnes System of Biomagnetic Technologies Incorporated," Neurosurgery, vol. 33, No. 2 (Aug. 1993), pp. 252-259.

Bergstrom et al. Stereotaxic Computed Tomography, Am. J. Roentgenol, vol. 127 pp. 167-170 (1976).

Bouazza-Marouf et al.; "Robotic-Assisted Internal Fixation of Femoral Fractures", IMECHE., pp. 51-58 (1995).

Brack et al., "Accurate X-ray Based Navigation in Computer-Assisted Orthopedic Surgery," CAR '98, pp. 716-722.

Brown, R., M.D., A Stereotactic Head Frame for Use with CT Body Scanners, Investigative Radiology .COPYRGT. J.B. Lippincott Company, pp. 300-304 (Jul.-Aug. 1979).

Bryan, "Bryan Cervical Disc System Single Level Surgical Technique", Spinal Dynamics, 2002, pp. 1-33.

Bucholz et al., "Variables affecting the accuracy of stereotactic localizationusing computerized tomography," Journal of Neurosurgery, vol. 79, Nov. 1993, pp. 667-673.

Bucholz, R.D., et al. Image-guided surgical techniques for infections and trauma of the central nervous system, Neurosurg. Clinics of N.A., vol. 7, No. 2, pp. 187-200 (1996).

Bucholz, R.D., et al., A Comparison of Sonic Digitizers Versus Light Emitting Diode-Based Localization, Interactive Image-Guided Neurosurgery, Chapter 16, pp. 179-200 (1993).

Bucholz, R.D., et al., Intraoperative localization using a three dimensional optical digitizer, SPIE—The Intl. Soc. for Opt. Eng., vol. 1894, pp. 312-322 (Jan. 17-19, 1993).

Bucholz, R.D., et al., Intraoperative Ultrasonic Brain Shift Monitor and Analysis, Stealth Station Marketing Brochure (2 pages) (undated).

Bucholz, R.D., et al., The Correction of Stereotactic Inaccuracy Caused by Brain Shift Using an Intraoperative Ultrasound Device, First Joint Conference, Computer Vision, Virtual Reality and Robotics in Medicine and Medical Robotics andComputer-Assisted Surgery, Grenoble, France, pp. 459-466 (Mar. 19-22, 1997).

Champleboux et al., "Accurate Calibration of Cameras and Range Imaging Sensors: The NPBS Method," IEEE International Conference on Robotics and Automation, Nice, France, May 1992.

Champleboux, "Utilisation de Fonctions Splines pour la Mise au Point D'un Capteur Tridimensionnel sans Contact," Quelques Applications Medicales, Jul. 1991.

Cinquin et al., "Computer Assisted Medical Interventions," IEEE Engineering in Medicine and Biology, May/Jun. 1995, pp. 254-263.

Cinquin et al., "Computer Assisted Medical Interventions," International Advanced Robotics Programme, Sep. 1989, pp. 63-65.

Clarysse et al., "A Computer-Assisted System for 3-D Frameless Localization in Stereotaxic MRI," IEEE Transactions on Medical Imaging, vol. 10, No. 4, Dec. 1991, pp. 523-529.

Cutting M.D. et al., Optical Tracking of Bone Fragments During Craniofacial Surgery, Second Annual International Symposium on Medical Robotics and Computer Assisted Surgery, pp. 221-225, (Nov. 1995).

Feldmar et al., "3D-2D Projective Registration of Free-Form Curves and Surfaces," Rapport de recherche (Inria Sophia Antipolis), 1994, pp. 1-44.

Foley et al., "Fundamentals of Interactive Computer Graphics," The Systems Programming Series, Chapter 7, Jul. 1984, pp. 245-266.

Foley et al., "Image-guided Intraoperative Spinal Localization," Intraoperative Neuroprotection, Chapter 19, 1996, pp. 325-340.

Foley, "The StealthStation: Three-Dimensional Image-Interactive Guidance for the Spine Surgeon," Spinal Frontiers, Apr. 1996, pp. 7-9.

Friets, E.M., et al. A Frameless Stereotaxic Operating Microscope for Neurosurgery, IEEE Trans. on Biomed. Eng., vol. 36, No. 6, pp. 608-617 (Jul. 1989).

Gallen, C.C., et al., Intracranial Neurosurgery Guided by Functional Imaging, Surg. Neurol., vol. 42, pp. 523-530 (1994).

Galloway, R.L., et al., Interactive Image-Guided Neurosurgery, IEEE Trans. on Biomed. Eng., vol. 89, No. 12, pp. 1226-1231 (1992).

Galloway, R.L., Jr. et al, Optical localization for interactive, image-guided neurosurgery, SPIE, vol. 2164, pp. 137-145 (undated.

Germano, "Instrumentation, Technique and Technology", Neurosurgery, vol. 37, No. 2, Aug. 1995, pp. 348-350.

Gildenberg et al., "Calculation of Stereotactic Coordinates from the Computed Tomographic Scan," Neurosurgery, vol. 10, No. 5, May 1982, pp. 580-586.

Gomez, C.R., et al., Transcranial Doppler Ultrasound Following Closed Head Injury: Vasospasm or Vasoparalysis?, Surg. Neurol., vol. 35, pp. 30-35 (1991).

Gonzalez, "Digital Image Fundamentals," Digital Image processing, Second Edition, 1987, pp. 52-54.

Gottesfeld Brown et al., "Registration of Planar Film Radiographs with Computer Tomography," Proceedings of MMBIA, Jun. 1996, pp. 42-51.

Grimson, W.E.L., An Automatic Registration Method for Frameless Stereotaxy, Image Guided Surgery, and enhanced Reality Visualization, IEEE, pp. 430-436 (1994).

Grimson, W.E.L., et al., Virtual-reality technology is giving surgeons the equivalent of x-ray vision helping them to remove tumors more effectively, to minimize surgical wounds and to avoid damaging critical tissues, Sci. Amer., vol. 280, No. 6,pp. 62-69 (Jun. 1999).

Gueziec et al., "Registration of Computed Tomography Data to a Surgical Robot Using Fluoroscopy: A Feasibility Study," Computer Science/Mathematics, Sep. 27, 1996, 6 pages.

Guthrie, B.L., Graphic-Interactive Cranial Surgery: The Operating Arm System, Handbook of Stereotaxy Using the CRW Apparatus, Chapter 13, pp. 193-211 (undated.

Hamadeh et al, "Kinematic Study of Lumbar Spine Using Functional Radiographies and 3D/2D Registration," TIMC UMR 5525-IMAG.

Hamadeh et al., "Automated 3-Dimensional Computed Tomographic and Fluorscopic Image Registration," Computer Aided Surgery (1998), 3:11-19.

Hamadeh et al., "Towards Automatic Registration Between CT and X-ray Images: Cooperation Between 3D/2D Registration and 2D Edge Detection," MRCAS '95, pp. 39-46.

Hardy, T., M.D., et al., CASS: A Program for Computer Assisted Stereotaxic Surgery, The Fifth Annual Symposium on Comptuer Applications in Medical Care, Proceedings, Nov. 1-4, 1981, IEEE, pp. 1116-1126, (1981).

Hatch, "Reference-Display System for the Integration of CT Scanning and the Operating Microscope," Thesis, Thayer School of Engineering, Oct. 1984, pp. 1-189.

Hatch, et al., "Reference-Display System for the Integration of CT Scanning and the Operating Microscope", Proceedings of the Eleventh Annual Northeast Bioengineering Conference, Mar. 14-15, 1985, pp. 252-254.

Heilbrun et al., "Preliminary experience with Brown-Roberts-Wells (BRW) computerized tomography stereotaxic guidance system," Journal of Neurosurgery, vol. 59, Aug. 1983, pp. 217-222.

Heilbrun, M.D., Progressive Technology Applications, Neurosurgery for the Third Millenium, Chapter 15, J. Whitaker & Sons, Ltd., Amer. Assoc. of Neurol. Surgeons, pp. 191-198 (1992).

Heilbrun, M.P., Computed Tomography—Guided Stereotactic Systems, Clinical Neurosurgery, Chapter 31, pp. 564-581 (1983).

Heilbrun, M.P., et al., Stereotactic Localization and Guidance Using a Machine Vision Technique, Sterotact & Funct. Neurosurg., Proceed. of the Mtg. of the Amer. Soc. for Sterot. and Funct. Neurosurg. (Pittsburgh, PA) vol. 58, pp. 94-98 (1992).

Henderson et al., "An Accurate and Ergonomic Method of Registration for Image-guided Neurosurgery," Computerized Medical Imaging and Graphics, vol. 18, No. 4, Jul.-Aug. 1994, pp. 273-277.

Hoerenz, "The Operating Microscope I. Optical Principles, Illumination Systems, and Support Systems," Journal of Microsurgery, vol. 1, 1980, pp. 364-369.

Hofstetter et al., "Fluoroscopy Based Surgical Navigation—Concept and Clinical Applications," Computer Assisted Radiology and Surgery, 1997, pp. 956-960.

Horner et al., "A Comparison of CT-Stereotaxic Brain Biopsy Techniques," Investigative Radiology, Sep.-Oct. 1984, pp. 367-373.

Hounsfield, "Computerized transverse axial scanning (tomography): Part 1. Description of system," British Journal of Radiology, vol. 46, No. 552, Dec. 1973, pp. 1016-1022.

International Search Report mailed Apr. 14, 1999 for PCT/US98/263495 which claims benefit of U.S. Appl. No. 60/069,595, filed Dec. 12, 1997.

Jacques et al., "A Computerized Microstereotactic Method to Approach, 3-Dimensionally Reconstruct, Remove and Adjuvantly Treat Small CNS Lesions," Applied Neurophysiology, vol. 43, 1980, pp. 176-182.

Jacques et al., "Computerized three-dimensional stereotaxic removal of small central nervous system lesion in patients," J. Neurosurg., vol. 53, Dec. 1980, pp. 816-820.

Japanese Office Action mailed Nov. 16, 2010 for Japanese patent application 2008-056669 which claims benefit of Japanese patent application 2000-523932, which claims benefit of WIPO patent application PCT/US1998/026395, filed Dec. 11, 1998; which claims benefit to U.S. Appl. No. 60/069,595, filed Dec. 12, 1997.

Joskowicz et al., "Computer-Aided Image-Guided Bone Fracture Surgery: Concept and Implementation," CAR '98, pp. 710-715.

Kall, B., The Impact of Computer and Imgaging Technology on Stereotactic Surgery, Proceedings of the Meeting of the American Society for Stereotactic and Functional Neurosurgery, pp. 10-22 (1987).

Kato, A., et al., A frameless, armless navigational system for computer-assisted neurosurgery, J. Neurosurg., vol. 74, pp. 845-849 (May 1991).

Kelly et al., "Computer-assisted stereotaxic laser resection of intraaxial brain neoplasms," Journal of Neurosurgery, vol. 64, Mar. 1986, pp. 427-439.

Kelly et al., "Precision Resection of Intra-Axial CNS Lesions by CT-Based Stereotactic Craniotomy and Computer Monitored CO2 Laser," Acta Neurochirurgica, vol. 68, 1983, pp. 1-9.

Kelly, P.J., Computer Assisted Stereotactic Biopsy and Volumetric Resection of Pediatric Brain Tumors, Brain Tumors in Children, Neurologic Clinics, vol. 9, No. 2, pp. 317-336 (May 1991).

Kelly, P.J., Computer-Directed Stereotactic Resection of Brain Tumors, Neurologica Operative Atlas, vol. 1, No. 4, pp. 299-313 (1991).

Kelly, P.J., et al., Results of Computed Tomography-based Computer-assisted Stereotactic Resection of Metastatic Intracranial Tumors, Neurosurgery, vol. 22, No. 1, Part 1, 1988, pp. 7-17 (Jan. 1988).

Kelly, P.J., Stereotactic Imaging, Surgical Planning and Computer-Assisted Resection of Intracranial Lesions: Methods and Results, Advances and Technical Standards in Neurosurgery, vol. 17, pp. 78-118, (1990).

Kim, W.S. et al., A Helmet Mounted Display for Telerobotics, IEEE, pp. 543-547 (1988).

Klimek, L., et al., Long-Term Experience with Different Types of Localization Systems in Skull-Base Surgery, Ear, Nose & Throat Surgery, Chapter 51, pp. 635-638 (undated).

Kosugi, Y., et al., An Articulated Neurosurgical Navigation System Using MRI and CT Images, IEEE Trans. on Biomed, Eng. vol. 35, No. 2, pp. 147-152 (Feb. 1988).

Krybus, W., et al., Navigation Support for Surgery by Means of Optical Position Detection, Computer Assisted Radiology Proceed. of the Intl. Symp. CAR '91 Computed Assisted Radiology, pp. 362-366 (Jul. 3-6, 1991).

Kwoh, Y.S., Ph.D., et al., A New Computerized Tomographic-Aided Robotic Stereotaxis System, Robotics Age, vol. 7, No. 6, pp. 17-22 (Jun. 1985).

Laitinen et al., "An Adapter for Computed Tomography-Guided, Stereotaxis," Surg. Neurol., 1985, pp. 559-566.

Laitinen, "Noninvasive multipurpose stereoadapter," Neurological Research, Jun. 1987, pp. 137-141.

Lavallee et al, "Matching 3-D Smooth Surfaces with their 2-D Projections using 3-D Distance Maps," SPIE, vol. 1570, Geometric Methods in Computer Vision, 1991, pp. 322-336.

Lavallee et al., "Computer Assisted Driving of a Needle into the Brain," Proceedings of the International Symposium Car '89, Computer Assisted Radiology, 1989, pp. 416-420.

Lavallee et al., "Computer Assisted Interventionist Imaging: The Instance of Stereotactic Brain Surgery," North-Holland MEDINFO 89, Part 1, 1989, pp. 613-617.

Lavallee et al., "Computer Assisted Spine Surgery: A Technique for Accurate Transpedicular Screw Fixation Using CT Data and a 3-D Optical Localizer," TIMC, Faculte de Medecine de Grenoble.

Lavallee et al., "Image guided operating robot: a clinical application in stereotactic neurosurgery," Proceedings of the 1992 IEEE Internation Conference on Robotics and Automation, May 1992, pp. 618-624.

Lavallee et al., "Matching of Medical Images for Computed and Robot Assisted Surgery," IEEE EMBS, Orlando, 1991.

Lavallee, "A New System for Computer Assisted Neurosurgery," IEEE Engineering in Medicine & Biology Society 11th Annual International Conference, 1989, pp. 0926-0927.

Lavallee, "VI Adaption de la Methodologie a Quelques Applications Cliniques," Chapitre VI, pp. 133-148.

Lavallee, S., et al., Computer Assisted Knee Anterior Cruciate Ligament Reconstruction First Clinical Tests, Proceedings of the First International Symposium on Medical Robotics and Computer Assisted Surgery, pp. 11-16 (Sep. 1994).

Lavallee, S., et al., Computer Assisted Medical Interventions, NATO ASI Series, vol. F 60, 3d Imaging in Medic., pp. 301-312 (1990).

Leavitt, D.D., et al., Dynamic Field Shaping to Optimize Stereotactic Radiosurgery, I.J. Rad. Onc. Biol. Physc., vol. 21, pp. 1247-1255 (1991).

Leksell et al., "Stereotaxis and Tomography—A Technical Note," ACTA Neurochirurgica, vol. 52, 1980, pp. 1-7.

Lemieux et al., "A Patient-to-Computed-Tomography Image Registration Method Based on Digitally Reconstructed Radiographs," Med. Phys. 21 (11), Nov. 1994, pp. 1749-1760.

Levin et al., "The Brain: Integrated Three-dimensional Display of MR and PET Images," Radiology, vol. 172, No. 3, Sep. 1989, pp. 783-789.

Maurer, Jr., et al., Registration of Head CT Images to Physical Space Using a Weighted Combination of Points and Surfaces, IEEE Trans. on Med. Imaging, vol. 17, No. 5, pp. 753-761 (Oct. 1998).

Mazier et al., "Computer-Assisted Interventionist Imaging: Application to the Vertebral Column Surgery," Annual International Conference of the IEEE Engineering in Medicine and Biology Society, vol. 12, No. 1, 1990, pp. 0430-0431.

Mazier et al., Chirurgie de la Colonne Vertebrale Assistee par Ordinateur: Appication au Vissage Pediculaire, Innov. Tech. Biol. Med., vol. 11, No. 5, 1990, pp. 559-566.

McGirr, S., M.D., et al., Stereotactic Resection of Juvenile Pilocytic Astrocytomas of the Thalamus and Basal Ganglia, Neurosurgery, vol. 20, No. 3, pp. 447-452, (1987).

Merloz, et al., "Computer Assisted Spine Surgery", Clinical Assisted Spine Surgery, No. 337, pp. 86-96.

Ng, W.S. et al., Robotic Surgery—A First-Hand Experience in Transurethral Resection of the Prostate Surgery, IEEE Eng. in Med. and Biology, pp. 120-125 (Mar. 1993).

Pelizzari et al., "Accurate Three-Dimensional Registration of CT, PET, and/or MR Images of the Brain," Journal of Computer Assisted Tomography, Jan./Feb. 1989, pp. 20-26.

Pelizzari et al., "Interactive 3D Patient-Image Registration," Information Processing in Medical Imaging, 12th International Conference, IPMI '91, Jul. 7-12, 136-141 (A.C.F. Colchester et al. eds. 1991).

Pelizzari et al., No. 528—"Three Dimensional Correlation of PET, CT and MRI Images," The Journal of Nuclear Medicine, vol. 28, No. 4, Apr. 1987, p. 682.

Penn, R.D., et al., Stereotactic Surgery with Image Processing of Computerized Tomographic Scans, Neurosurgery, vol. 3, No. 2, pp. 157-163 (Sep.-Oct. 1978).

Phillips et al., "Image Guided Orthopaedic Surgery Design and Analysis," Trans Inst. MC, vol. 17, No. 5, 1995, pp. 251-264.

Pixsys, 3-D Digitizing Accessories, by Pixsys (marketing brochure)(undated) (2 pages).

Potamianos et al., "Intra-Operative Imaging Guidance for Keyhole Surgery Methodology and Calibration," First International Symposium on Medical Robotics and Computer Assisted Surgery, Sep. 22-24, 1994, pp. 98-104.

Reinhardt et al., "CT-Guided 'Real Time' Stereotaxy," ACTA Neurochirurgica, 1989.

Reinhardt, H., et al., A Computer-Assisted Device for Intraoperative CT-Correlated Localization of Brain Tumors, pp. 51-58 (1988).

Reinhardt, H.F. et al., Sonic Stereometry in Microsurgical Procedures for Deep-Seated Brain Tumors and Vascular Malformations, Neurosurgery, vol. 32, No. 1, pp. 51-57 (Jan. 1993).

Reinhardt, H.F., et al., Mikrochirugische Entfernung tiefliegender Gefa.beta.mi.beta.bildungen mit Hilfe der Sonar-Stereometrie (Microsurgical Removal of Deep-Seated Vascular Malformations Using Sonar Stereometry). Ultraschall in Med. 12, pp. 80-83(1991).

Reinhardt, Hans. F., Neuronavigation: A Ten-Year Review, Neurosurgery, pp. 329-341 (undated).

Roberts et al., "A frameless stereotaxic integration of computerized tomographic imaging and the operating microscope," J. Neurosurg., vol. 65, Oct. 1986, pp. 545-549.

Rosenbaum et al., "Computerized Tomography Guided Stereotaxis: A New Approach," Applied Neurophysiology, vol. 43, No. 3-5, 1980, pp. 172-173.

Sautot, "Vissage Pediculaire Assiste Par Ordinateur," Sep. 20, 1994.

Schueler et al., "Correction of Image Intensifier Distortion for Three-Dimensional X-Ray Angiography," SPIE Medical Imaging 1995, vol. 2432, pp. 272-279.

Selvik et al., "A Roentgen Stereophotogrammetric System," Acta Radiologica Diagnosis, 1983, pp. 343-352.

Shelden et al., "Development of a computerized microsteroetaxic method for localization and removal of minute CNS lesions under direct 3-D vision," J. Neurosurg., vol. 52, 1980, pp. 21-27.

Simon, D.A., Accuracy Validation in Image-Guided Orthopaedic Surgery, Second Annual Intl. Symp. on Med. Rob. an Comp-Assisted surgery, MRCAS '95, pp. 185-192 (undated).

Smith et al., "Computer Methods for Improved Diagnostic Image Display Applied to Stereotactic Neurosurgery," Automedical, vol. 14, 1992, pp. 371-382 (4 unnumbered pages).

Smith et al., "The Neurostation.TM.—A Highly Accurate, Minimally Invasive Solution to Frameless Stereotactic Neurosurgery," Computerized Medical Imaging and Graphics, vol. 18, Jul.-Aug. 1994, pp. 247-256.

Smith, K.R., et al. Multimodality Image Analysis and Display Methods for Improved Tumor Localization in Stereotactic Neurosurgery, Annul Intl. Conf. of the IEEE Eng. in Med. and Biol. Soc., vol. 13, No. 1, p. 210 (1991).

Tan, K., Ph.D., et al., A frameless stereotactic approach to neurosurgical planning based on retrospective patient-image registration, J Neurosurgy, vol. 79, pp. 296-303 (Aug. 1993).

The Laitinen Stereotactic System, E2-E6.

Thompson, et al., A System for Anatomical and Functional Mapping of the Human Thalamus, Computers and Biomedical Research, vol. 10, pp. 9-24 (1977).

Trobaugh, J.W., et al., Frameless Stereotactic Ultrasonography: Method and Applications, Computerized Medical Imaging and Graphics, vol. 18, No. 4, pp. 235-246 (1994).

Viant et al., "A Computer Assisted Orthopaedic System for Distal Locking of Intramedullary Nails," Proc. of MediMEC '95, Bristol, 1995, pp. 86-91.

Von Hanwhr et al., Foreword, Computerized Medical Imaging and Graphics, vol. 18, No. 4, pp. 225-228, (Jul.-Aug. 1994).

Wang, M.Y., et al., An Automatic Technique for Finding and Localizing Externally Attached Markers in CT and MR Volume Images of the Head, IEEE Trans. on Biomed. Eng., vol. 43, No. 6, pp. 627-637 (Jun. 1996).

Watanabe et al., "Three-Dimensional Digitizer (Neuronavigator): New Equipment for Computed Tomography-Guided Stereotaxic Surgery," Surgical Neurology, vol. 27, No. 6, Jun. 1987, pp. 543-547.

Watanabe, "Neuronavigator," Igaku-no-Ayumi, vol. 137, No. 6, May 10, 1986, pp. 1-4.

Watanabe, E., M.D., et al., Open Surgery Assisted by the Neuronavigator, a Stereotactic, Articulated, Sensitive Arm, Neurosurgery, vol. 28, No. 6, pp. 792-800 (1991).

Weese et al., "An Approach to 2D/3D Registration of a Vertebra in 2D X-ray Fluoroscopies with 3D CT Images," pp. 119-128.

\* cited by examiner

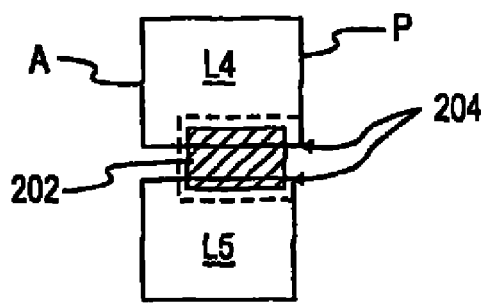
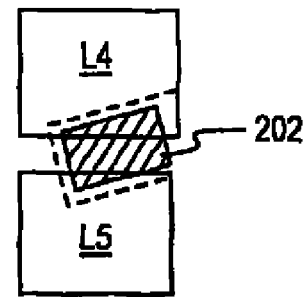
FIG. 4A  FIG. 4B
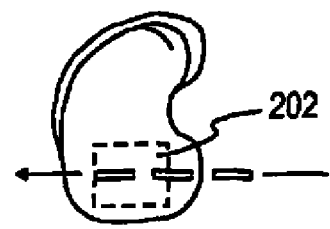
FIG. 5A
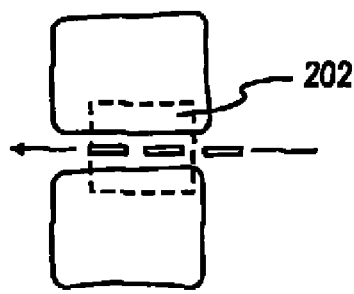
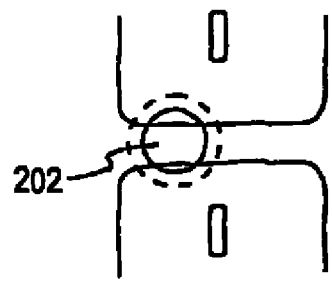
FIG. 5B  FIG. 5C

IMAGE GUIDED SPINAL SURGERY GUIDE SYSTEM AND METHOD FOR USE THEREOF

CROSS-REFERENCE TO RELATED APPLICATIONS

This application is a divisional of U.S. patent application Ser. No. 10/939,953 filed on Sep. 13, 2004, now U.S. Pat. No. 7,763,035, issued on Jul. 27, 2010, which is a continuation of U.S. patent application Ser. No. 09/992,546 filed on Nov. 6, 2001 which is now U.S. Pat. No. 6,796,988 issued on Sep. 28, 2004, which is a continuation of U.S. patent application Ser. No. 09/209,248 filed on Dec. 10, 1998 which is now U.S. Pat. No. 6,348,058 issued on Feb. 19, 2002, which claims benefit of U.S. Patent Application No. 60/069,595 filed on Dec. 12, 1997. The disclosures of the above applications are incorporated herein by reference.

FIELD OF THE INVENTION

The present invention relates generally to providing a guide for use in performing spinal surgery, in conjunction with systems that use and generate images during medical and surgical procedures, which images assist in executing the procedures and indicate the relative position of various body parts and surgical instruments. In particular the invention relates to a guide, and system and method utilizing the guide, for performing spinal surgery to provide protected access across a spinal disc and into adjacent vertebrae to prepare an implantation space so as to ensure predetermined trajectory and placement of an artificial implant/bone dowel into the implantation space.

BACKGROUND OF THE INVENTION

Various instruments and methods have been used to prepare adjacent vertebrae of the spine for insertion of a bone dowel or artificial implant. These instruments and methods allow for the removal of disc material from between adjacent vertebrae as well as a portion of each vertebra to form an implantation space or opening. Drill sleeve, tubular member, sheath, working channel, and guard are a few of the names for the protective guide used to guide drills and other disc and bone removal devices into the spine to form the implantation space for receipt of the bone dowel or artificial implant. Certain of the guides have a sharpened end or include teeth for engaging the vertebrae upon application of an impaction force. The guide can be positioned so as to span the disc space and be seated into the adjacent vertebrae to provide protected access to the spine during the process of forming the implantation space. The implantation space spans the disc space and protrudes into each of the adjacent vertebrae along two opposed resected arcs. An example of the procedure for drilling holes across a disc space and instrumentation pertaining thereto are described in U.S. Pat. No. 5,484,437 to Michelson and is incorporated herein by reference.

The use of cylindrical implants is desirable because the surgeon can prepare the recipient site by drilling a cylindrical hole across the disc space and into the adjacent vertebrae. The curved surface of the cylindrical holes drilled into the vertebrae provide for the possibility of tight congruency when the cylindrical hole is fitted with an implant having corresponding cylindrical portions of matched diameter.

Typically, threaded artificial implants, such as the implant disclosed in U.S. Pat. No. 5,015,247 to Michelson, the entire disclosure of which is incorporated herein by reference, are placed into the implantation space between the adjacent vertebrae to directly participate and be incorporated in the ensuing fusion. Threaded bone dowels, such as those taught by Viche may also be placed into the implantation space for the purpose of bridging the opening and to be incorporated into the fusion between the vertebrae. Moreover, artificial implants of the push-in type, such as those disclosed in U.S. Pat. No. 5,593,409 to Michelson and assigned to the assignee of the present application and incorporated herein by reference, may also be inserted into the implantation space formed by the above described instruments and methods.

Whether pushing or threading an implant or dowel into the implantation space, the surgeon attempts to orient the sheath for guiding the formation of the implantation space to remove approximately the same amount of material from each of the vertebra. Once the implant or dowel is implanted, a fluoroscope may be used to assist in determining if proper placement has occurred.

A number of different types of surgical navigation systems have been described that include indications of the relative positions of medical instruments and body parts used in medical or surgical procedures. For example, U.S. Pat. No. 5,383,454 to Bucholz; PCT Application No. PCT/US94/04530 (Publication No. WO 94/24933) to Bucholz; and PCT Application No. PCT/US95/12894 (Publication No. WO 96/11624) to Bucholz et al., the entire disclosures of which are incorporated herein by reference, disclose systems for use during a medical or surgical procedure using scans generated by a scanner prior to the procedure. Surgical navigation systems typically include tracking means such as for example an LED array on the body part, emitters on the medical instruments, a digitizer to track the positions of the body part and the instruments, and a display for the position of an instrument used in a medical procedure relative to a body part.

Procedures for preparing an implantation space in the spine present certain particular challenges to be addressed at specific levels within the spinal column. For example, preforming such a procedure at L4-5 of the spine can raise the following issues: 1) During a posterior approach, significant muscle stripping and tearing is required to reach the L4-5 disc space. Significant post-operative trauma to the patient may result. 2) During an anterior approach, with either a transperitoneal or retroperitoneal, open or laparoscopic approach to the L4-5 disc space, the great vessels lie almost directly on the front of the spinal column at that level. Dissection and manipulation of these vessels may be time-consuming and difficult.

The applicant determined that a retroperitoneal "oblique approach" to the L-5 disc space can present a preferred surgical solution. The muscle splitting and tearing of the posterior approach is therefore not inevitable, since the oblique approach takes place just anterior to the psoas muscle located laterally along the vertebral column. The oblique approach also allows for an approach slightly posterior of the great vessels lying anterior on the spinal column, thus reducing any risk of injury to the great vessels.

In viewing the spine solely from a lateral fluoro image, the spine surgeon, via this oblique approach, would have a limited ability to see an indication of the depth and direction of their instrumentation as it moves in a posterior lateral fashion across the disc space towards the exiting nerve root.

In light of the foregoing, it would be beneficial in the art for a system and method for the placement of a guide in the spine that provides directional assistance to the surgeon to improve the placement of the guide used in forming the implantation space as well as for use in determining the depth of insertion of instruments passing through the guide, thereby improving the placement of implants and dowels into the implantation space.

SUMMARY OF THE INVENTION

Accordingly, the present invention is directed to a guide, system, and method for using the guide in performing spinal surgery to prepare an implantation space across a spinal disc and adjacent vertebrae. More specifically, one object of the present invention is directed to apparatus and procedures for the placement of a guide into the spine using image guided surgery to improve proper placement of the guide through which the implantation space is to be formed and thus proper placement of the implant or dowel.

To achieve this object and other advantages and in accordance with the purpose of the invention, as embodied and broadly described herein, the invention includes a guide for use in performing spinal surgery to prepare an implantation space across a spinal disc and adjacent vertebrae. The guide is used in conjunction with a computer controlled surgical navigation system employing an energy-detecting array to track positions of the guide in three dimensional space relative to a known reference point. The guide comprises a body for providing protected access to prepare the implantation space across the spinal disc and into the adjacent vertebrae. The body has a passage adapted to receive a bone removal device for forming the implantation space through the body. At least one emitter array is attached to the body for use in identifying the location of the guide relative to the adjacent vertebrae.

The guide may additionally include a disc penetrating extension extending from the body for insertion into the disc space between the adjacent vertebrae and for bearing against endplates of the adjacent vertebrae. A preferred body includes a hollow tube having an end including extensions for penetrating the spine. An emitter array is preferably on each extension of the guide and more preferably includes at least one LED. Preferred arrays include an electrically energizable energy emitter array, known as an active emitter, as well as a reflective surface that reflects signals, known as a passive emitter.

Additionally, the invention includes a system for use in performing spinal surgery to prepare across a spinal disc and adjacent vertebrae an implantation space. The system comprises the above described guide and a computer controlled surgical navigation system employing an energy detecting array to track positions of the guide in three dimensional space relative to a known reference point.

In addition, the invention further comprises a method for performing spinal surgery with a guide used to provide protected access across a spinal disc and into adjacent vertebrae to prepare an implantation space. The method comprises the steps of: attaching a reference array to the vertebrae of interest; registering the location of that vertebrae with a computer controlled surgical navigation system; contacting one end of the guide having at least one emitter array attached thereto to the adjacent vertebrae; employing the surgical navigation system with a computer controller and a digitizer array for communicating with the energy emitter of the guide; positioning the guide in three dimensional space relative to a known reference point system; and forming the implantation space through the guide across the disc space and into a portion of each of the adjacent vertebrae.

In another aspect, the method includes the step of generating a display of the position of the guide. The generating step preferably displays the location of the guide relative to the adjacent vertebrae to provide a view of the axial orientation of the guide relative to each vertebra and/or relative to the adjacent vertebrae. The orientation of the disc penetrating extensions can also be displayed. The location of the tip of an instrument which is placed through the guide can be displayed as well. Identifying the location of the instrument tip passing through the guide permits tracking of tool depth insertion. The generating step may also display the location of the guide relative to the adjacent vertebrae to provide a cross-sectional view of the guide relative to one of an anterior or posterior view of the adjacent vertebrae.

The method may also include the step of emitting a signal from an emitter attached to the guide which is received by an apparatus representatively indicating that signal on a visual display. A preferred method of the present invention also includes the step of implanting an artificial implant, a bone dowel, or other type of bone into the implantation space. The method also may include the step of tracking an artificial implant or bone dowel inserter via an emitter array attached to the inserter. The inserter preferably is configured to pass through the guide. The computer controlled surgical navigation system may be configured to display the inserter as it passes through the guide and more preferably may display both the inserter and the attached artificial implant or bone dowel based on the geometrical configuration of the inserter and of an implant or bone dowel attached thereto.

The objects of the invention are to provide a surgeon with the guide, system, and method to track the guide used in conjunction with a surgical navigation system in such a manner to operate on a patient on the spine to ensure proper orientation of the guide to the spine when forming an implantation space.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in this description.

It is to be understood that both the foregoing general description and the following detailed description are exemplary and explanatory only and are not restrictive of the invention.

BRIEF DESCRIPTION OF THE DRAWINGS

The accompanying drawings, which are incorporated in and constitute a part of this specification, illustrate one embodiment of the invention and together with the description, serve to explain the principles of the invention.

FIG. 4A is a cross-sectional view of a spinal segment having an implant or dowel in a desirable position within the disc space and vertebral endplates;

FIG. 4B is a cross-sectional view of a spinal segment having an implant or dowel in a generally less desirable position within the disc space and vertebral endplates;

FIG. 5A is a cross-sectional view of an implant or dowel projected over an axial top view of a vertebra and showing a predetermined axial alignment of the implant or dowel to the vertebra;

FIG. 5B is a cross-sectional view of an implant or dowel positioned between adjacent vertebrae and showing a predetermined sagittal alignment of the implant or dowel to the vertebrae;

FIG. 5C is a cross-sectional view of an implant or dowel positioned between adjacent vertebrae and showing a predetermined coronal alignment of the implant or dowel to the vertebrae;

DETAILED DESCRIPTION OF THE PREFERRED EMBODIMENT

Reference will now be made in detail to the present preferred embodiment of the invention, an example of which is illustrated in the accompanying drawings. Wherever possible, the same reference numbers will be used throughout the drawings to refer to the same or like parts. The following example is intended to be purely exemplary of the invention.

Figure 1:
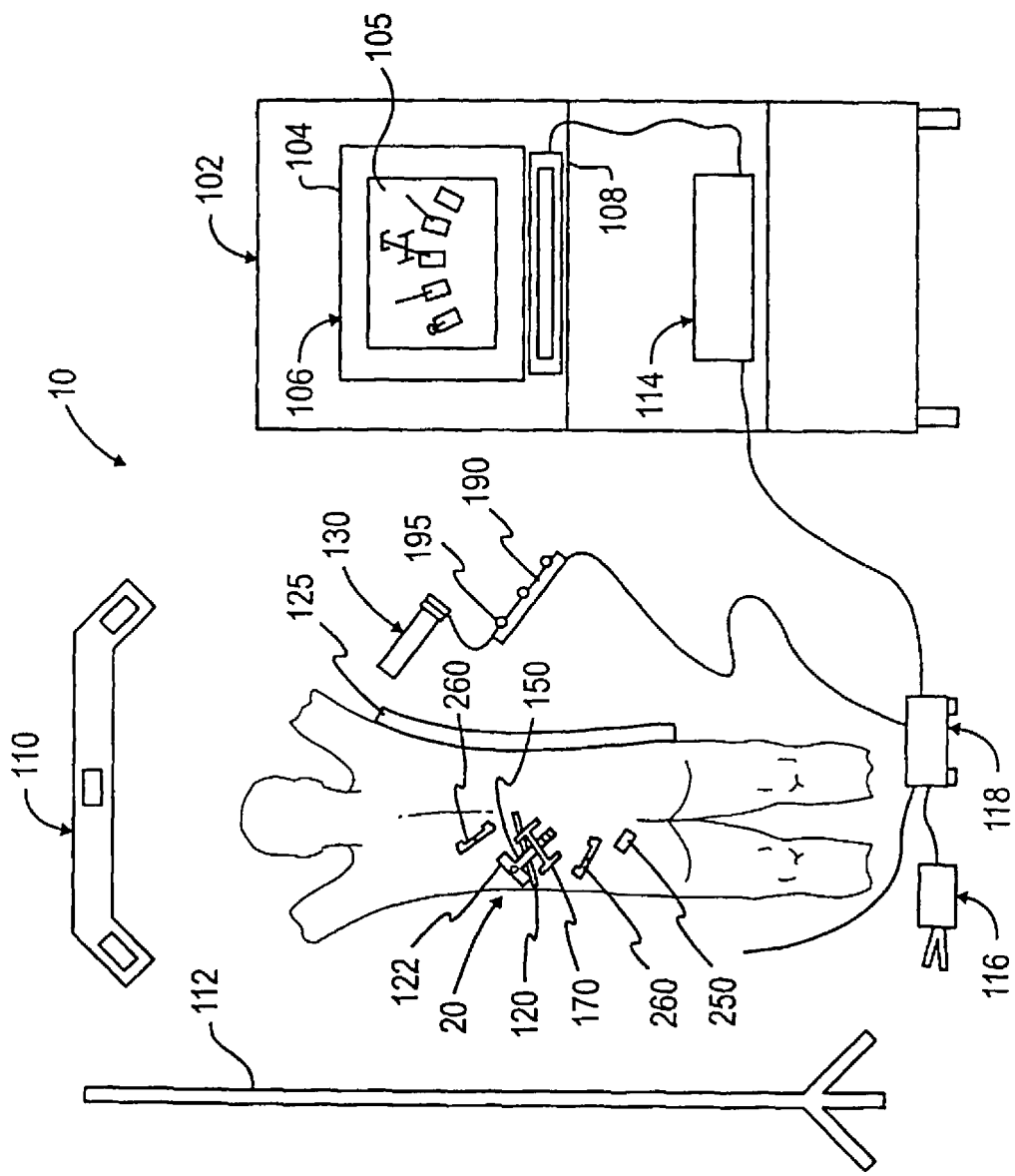
FIG. 1 is a schematic diagram of one preferred embodiment of a system, including a guide, a reference arc, a post, and wires placed in the spine for use with a surgical navigation system for spinal surgical procedures.

As generally described in PCT/US95/12894, the entire disclosure of which is incorporated herein by reference, a typical surgical navigation system is shown in FIG. 1. A computer assisted image guided surgery system, indicated generally at 10, generates an image for display on a monitor 106 representing the position of one or more body elements, such as spinal elements fixedly held in a stabilizing frame or device such as a spinal surgery frame 125 commonly used for spinal surgery. A reference arc 120 bearing tracking means such as for example LED emitters 122 is mounted to the spinous process by a clamp or other connecting device. The image is generated from an image data set, usually generated preoperatively by a CAT scanner for example, which image has reference points for at least one body element, such as a spinal element. The reference points of the particular body element have a fixed spatial relation to the particular body element. The system includes an apparatus such as a digitizer or other Position Sensing Unit (PSU), such as for example sensor array 110 on support 112 for identifying, during the procedure, the relative position of each of the reference points to be displayed by tracking the position of emitters 122 on arc 120. The system also includes a processor 114 such as a PC or other suitable workstation processor associated with controller 108 for modifying the image data set according to the identified relative position of each of the reference points during the procedure, as identified by array 110. The processor 114 can then, for example, generate a displaced image data set representing the position of the body elements during the procedure for display on monitor 106. In summary, the operation of a surgical navigating system is well known in the art and need not further be described here.

An embodiment of the present invention permits tracking without use of a clamp or other connecting device holding an emitter to a vertebral body by use of dynamic referencing (e.g. fluoroscopy referencing, magnetic resonance imaging intraoperatively, and ultrasonic registration). All of these options will show real time displacement and manipulation of the spine.

Figure 2:
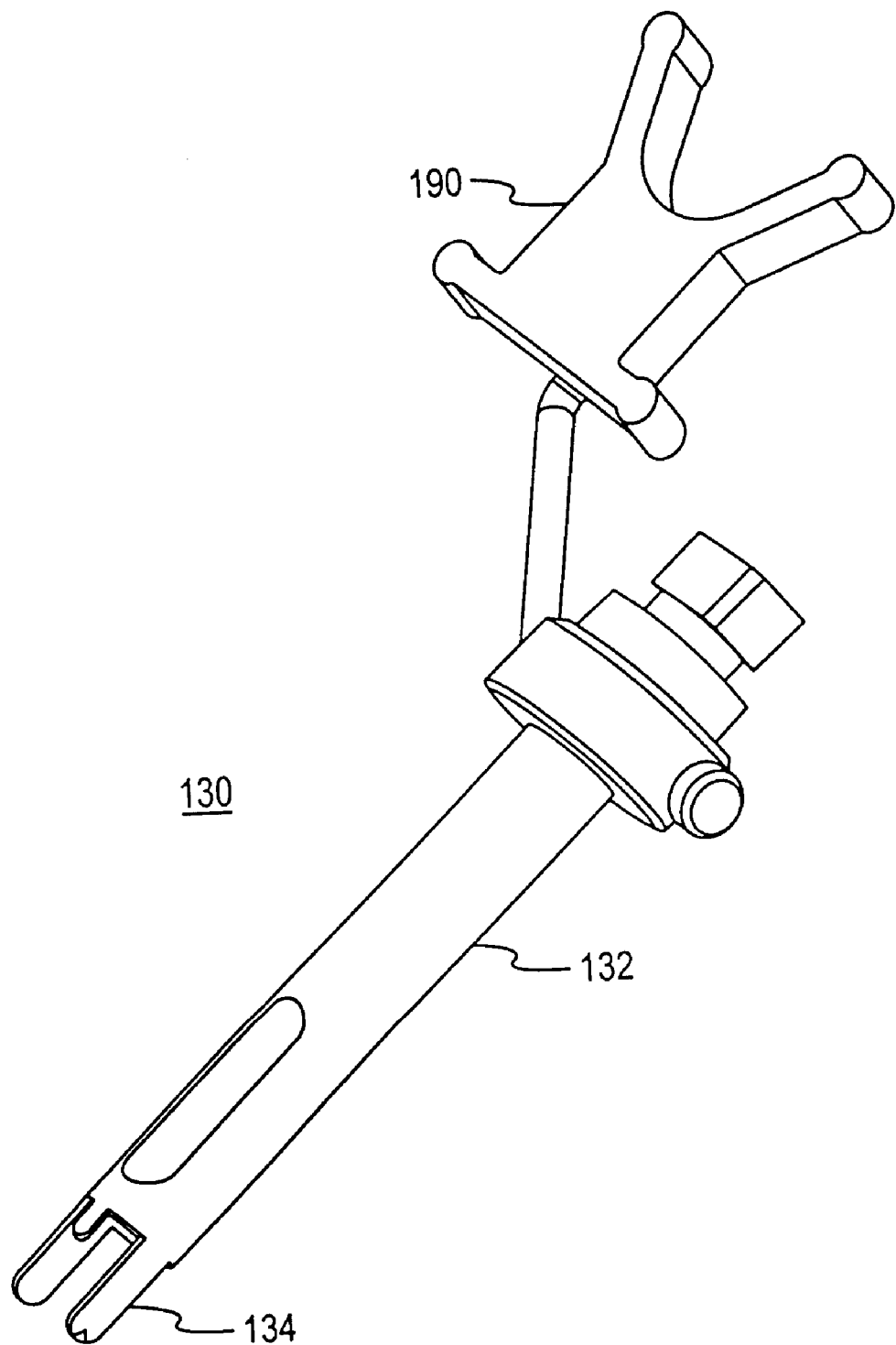
FIG. 2 is a perspective view of one preferred embodiment of a guide according to the present invention.
Figure 3:
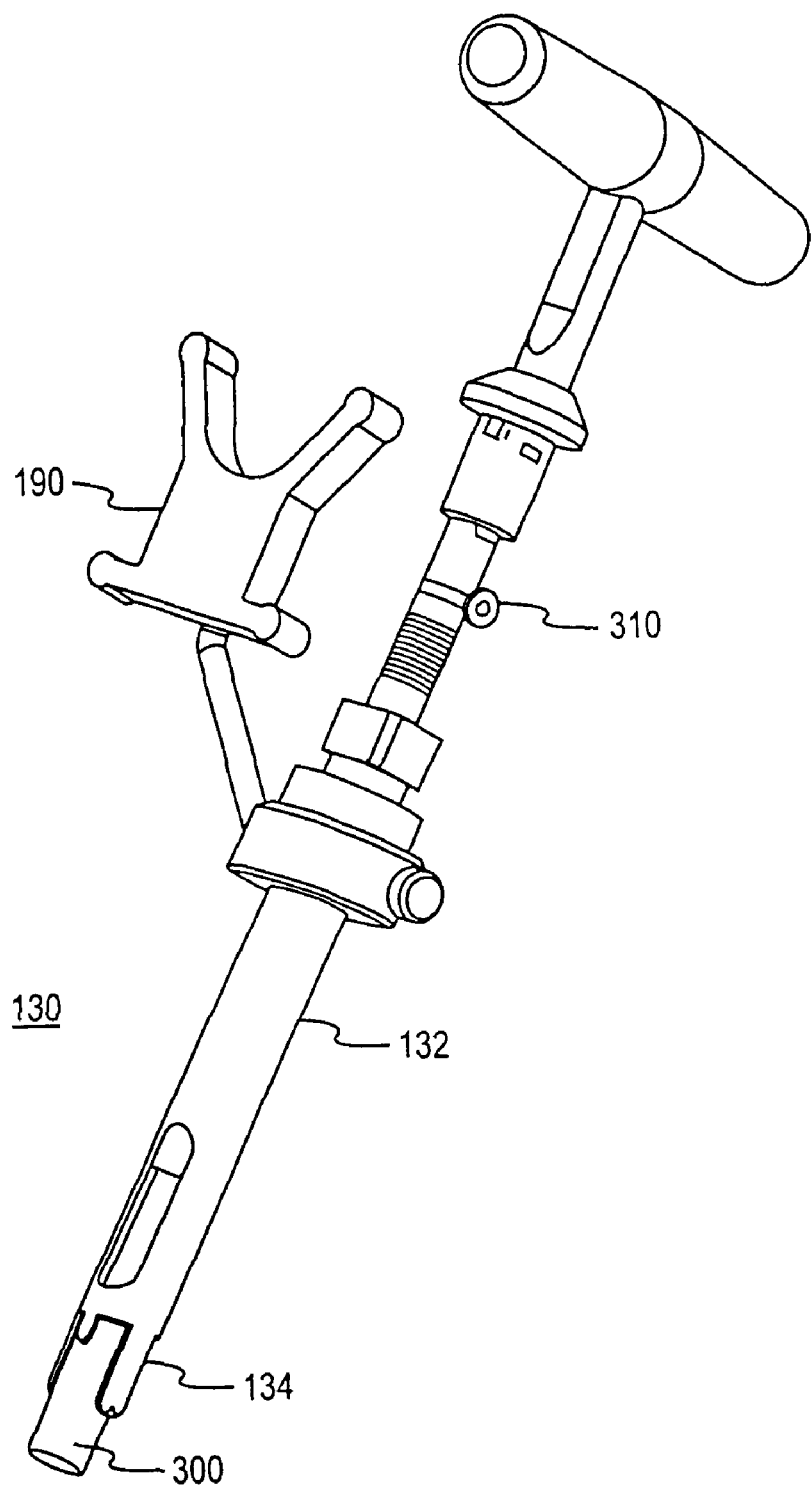
FIG. 3 is a perspective view of the guide of FIG. 2 with an instrument having an LED passing through the guide.
Figure 10:
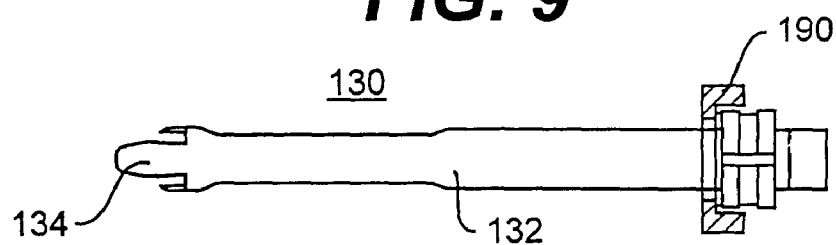
FIG. 10 is a side view of a guide having a disc penetrating extension and prong for engaging the adjacent vertebrae with attached emitter in cross-section.

In accordance with the preferred embodiment of the present invention, with further reference to FIGS. 2 and 3, the invention includes guide 130 for use in performing spinal surgery to prepare across a spinal disc and adjacent vertebrae an implantation space. Guide 130 is used in conjunction with computer controlled surgical navigation system 10 employing energy-detecting array 110 to track positions of guide 130 in three dimensional space relative to a known reference point. Guide 130 comprises body 132 for providing protected access to prepare the implantation space across the spinal disc and into the adjacent vertebrae. Body 132 has a passage adapted to receive a bone removal device, as shown in FIG. 3, for forming the implantation space through body 132. At least one emitter array 190 is attached to body 132 for use in identifying the location of guide 130 relative to the adjacent vertebrae. FIG. 10 shows an alternative guide 130 with disc penetrating extensions 134 and attached emitter array 190.

Figure 6A:
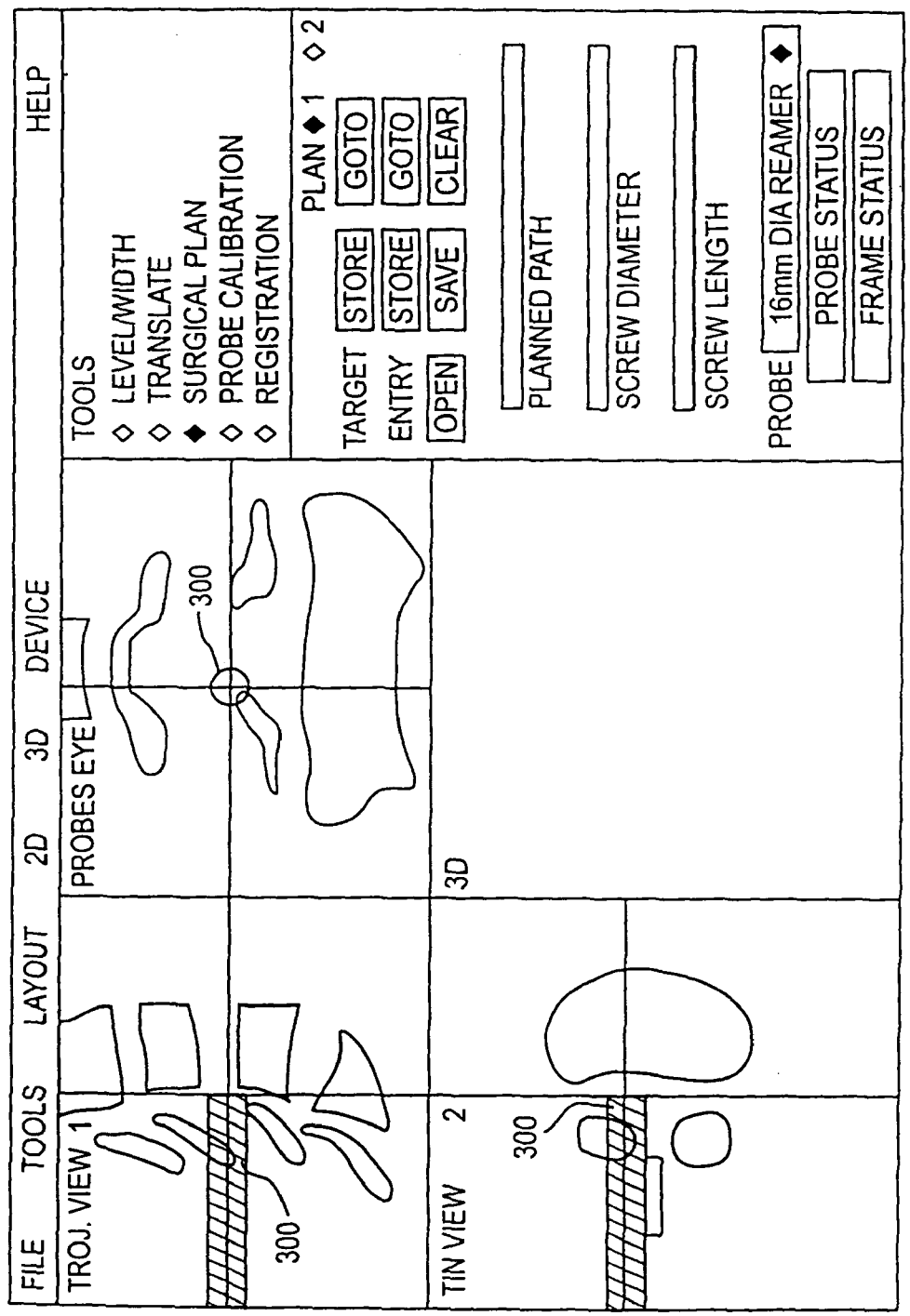
FIG. 6A depicts an image on a display screen produced in association with the guide, reamer passing through the guide, and surgical navigation system in accordance with a preferred embodiment of the present invention.
Figure 6B:
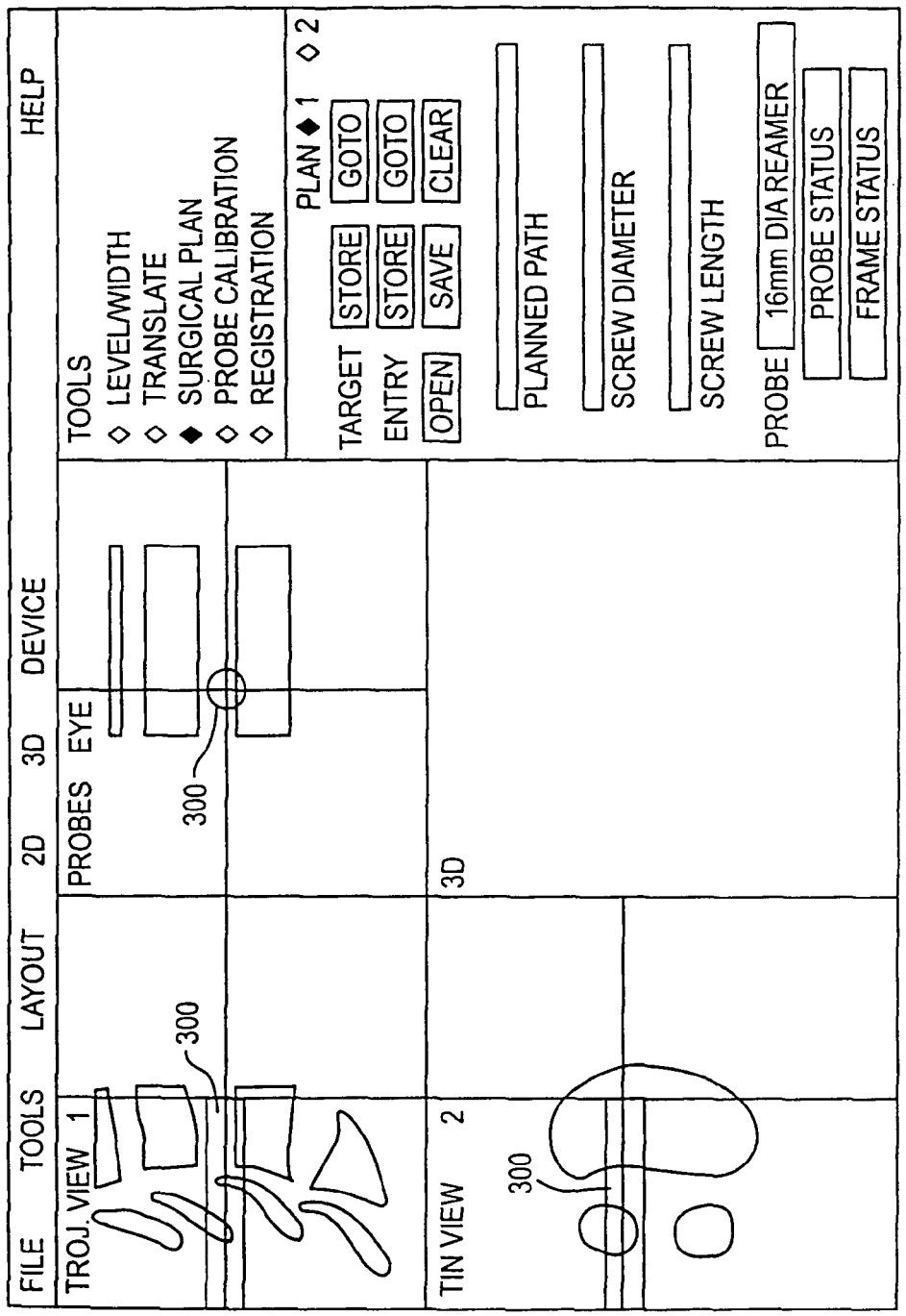
FIG. 6B depicts the embodiment of FIG. 6A with the reamer inserted deeper into the spine intervertebral disc space.

A preferred bone removal device includes a reamer 300 having a LED 310 as shown in FIGS. 3, 6A, and 6B. A visual display of the reamer 300 may be generated showing the depth of insertion of the reamer 300 into the spine relative to the known coordinates of the guide 130 and the body into which reamer 300 penetrates.

Figure 9:
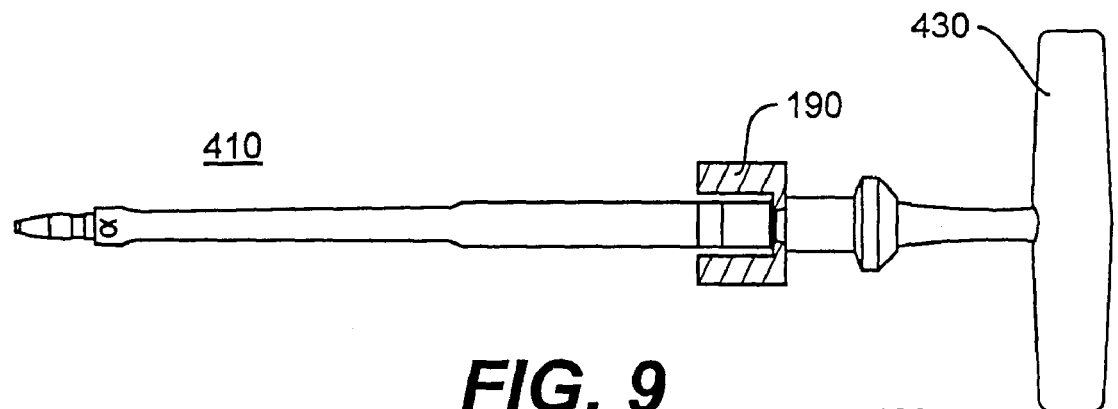
FIG. 9 is a side view of a distractor and T-handle assembly with attached emitter in cross-section.
Figure 11A:
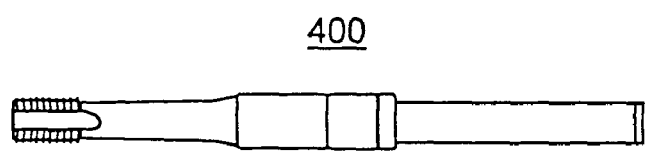
FIG. 11A is a side view of a tap.
Figure 11B:
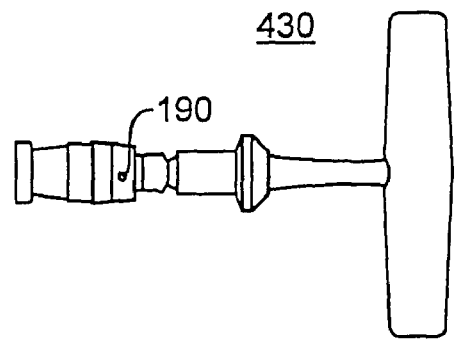
FIG. 11B is a side view of a T-handle With emitter.
Figure 12:
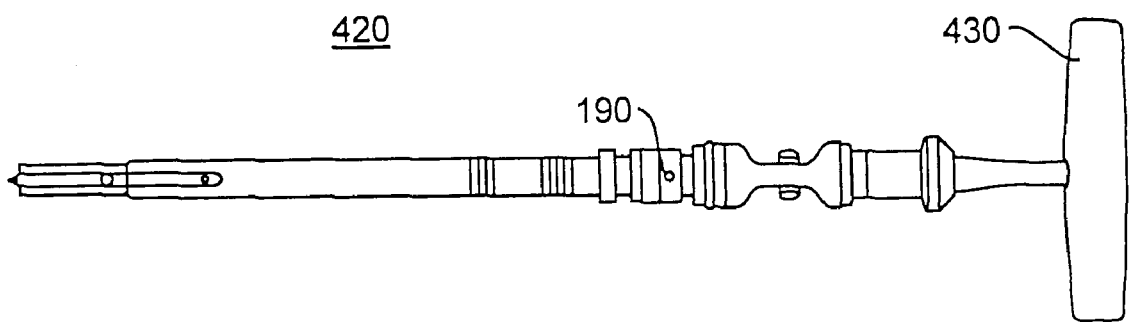
FIG. 12 is a side view of an inserter with attached T-handle and emitter.

Other devices for use in performing spinal surgery across the disc space are shown FIGS. 9, 11A, 11B, and 12. FIG. 9 depicts a distractor 410 with attached T-handle 430 and emitter 190. FIG. 11A shows a tap 400 which is preferably adapted for attachment to T-handle 430 shown in FIG. 11B. T-handle 430 includes an emitter 190 attached thereto for use in identifying the location of tap 400 relative to the adjacent vertebrae into which it is inserted. FIG. 12 shows an inserter 420 with attached T-handle 430 and emitter array 190. Emitter 190 on distractor 410, tap 400, and inserter 420, respectively is used to identify the location of each tool in three dimensional space relative to a known reference point so that each may be individually shown on the visual display associated with computer controlled surgical navigation system 10.

Guide 130 may additionally include a disc penetrating extension extending from body 132 for insertion into the disc space between the adjacent vertebrae and for bearing against endplates of the adjacent vertebrae. A preferred body 132 includes a hollow tube having an end including extensions 134 for penetrating the spine. A preferred emitter array 190 on the guide are light emitting diodes ("LEDs"), but can be any other energy radiating device or tracking means known in the art capable of being tracked by a corresponding detector array. A preferred emitter array includes three LEDs for use in determining location and rotation of a tool in space in all directions. For purposes of illustration, not limitation, the tracking means may generate signals actively such as with acoustic, magnetic, electromagnetic, radiologic, and micropulsed radar systems, or passively such as with reflective surfaces.

Additionally, the invention includes a system for use in performing spinal surgery to prepare across a spinal disc and adjacent vertebrae an implantation space. The system comprises the above described guide 130 and computer controlled surgical navigation system 10 employing an energy detecting array 110 to track positions of guide 130 in three dimensional space relative to a known reference point in a body similarly tracked by sensor array 110.

Guide 130 and computer controlled surgical navigation system 10 enable the spine surgeon to ensure the proper implantation of an implant or dowel by forming a properly oriented implantation space through guide 130 and into the spine as well as observe the depth of invention of instruments passing through guide 130. This outcome is ensured by properly orienting guide 130 prior to forming the implantation space. FIG. 4A shows a cross-sectional view of a spinal segment 200 having an implant or dowel 202 in a predetermined endplate 204 engagement. Typically, the preferred predetermined endplate 204 engagement occurs when approximately equal amounts of bone are removed from each of the adjacent endplates 204 of the adjacent vertebrae and the implant or dowel 202 is axially aligned from anterior A to posterior P or vise versa.

A cross-sectional view of a spinal segment having an implant or dowel 202 in a generally less desirable position is shown in FIG. 4B. The implant or dowel 202 depicted in FIG. 4B is shown implanted in an implantation space having an angled sagittal trajectory. In contrast, a generally preferred predetermined sagittal alignment of the implant or dowel 202 to the vertebrae is shown in FIG. 5B.

FIG. 5A shows a cross-sectional view of an implant or dowel 202 projected over an axial section of a vertebra and showing a predetermined axial alignment of the implant or dowel 202 to the vertebra from the posterior to the anterior. FIG. 5C is a cross-sectional view of an implant or dowel 202 positioned between adjacent vertebrae and showing a predetermined coronal alignment of the implant or dowel 202 to the vertebra. The proper placement of guide 130 prior to forming the implantation space enables the implant 202 to be placed in a predetermined axial, sagittal, and coronal orientation as depicted in FIGS. 5A, 5B, and 5C.

Once the surgeon registers the vertebral body with computer controlled surgical navigation system 10, the location of the above disclosed guide 130 can be viewed on the computer system relative to that body so that the spine surgeon can see in real time the location of the end of guide 130 in an axial, coronal, and sagittal view, as well as in a 3-D reconstruction. The surgeon will also be able to view the trajectory of guide 130 relative to this body in all three places. This technique clearly enhances the process for the surgeon to position guide 130 to form an implantation space and thereby optimize the positioning of the implant or dowel to be inserted.

In accordance with the display screens depicted in FIGS. 6A, 6B, 7, and 8, once a reference array is attached to the patient and registered, software within navigational system 10 provides the following information to the surgeon. The location of guide 130 is shown relative to the anatomy of the patient. The rotational position of guide 130 is also indicated to allow the surgeon to observe the orientation of guard extensions 134 relative to the adjacent vertebrae of the spine.

In particular, FIGS. 6A and 6B display reamer 300 inserted through guide 130 and show the depth of penetration of reamer 300. FIG. 6A shows reamer 300 just prior to removing material from the vertebrae endplates. FIG. 6B shows reamer 300 at a greater depth of insertion and after removal of material from the vertebrae endplates. The final position of reamer 300 remains on the display screen for reference by the surgeon. The diameter of the reamer 300 is preferably entered into the computer or selected from a programmed menu.

Figure 7:
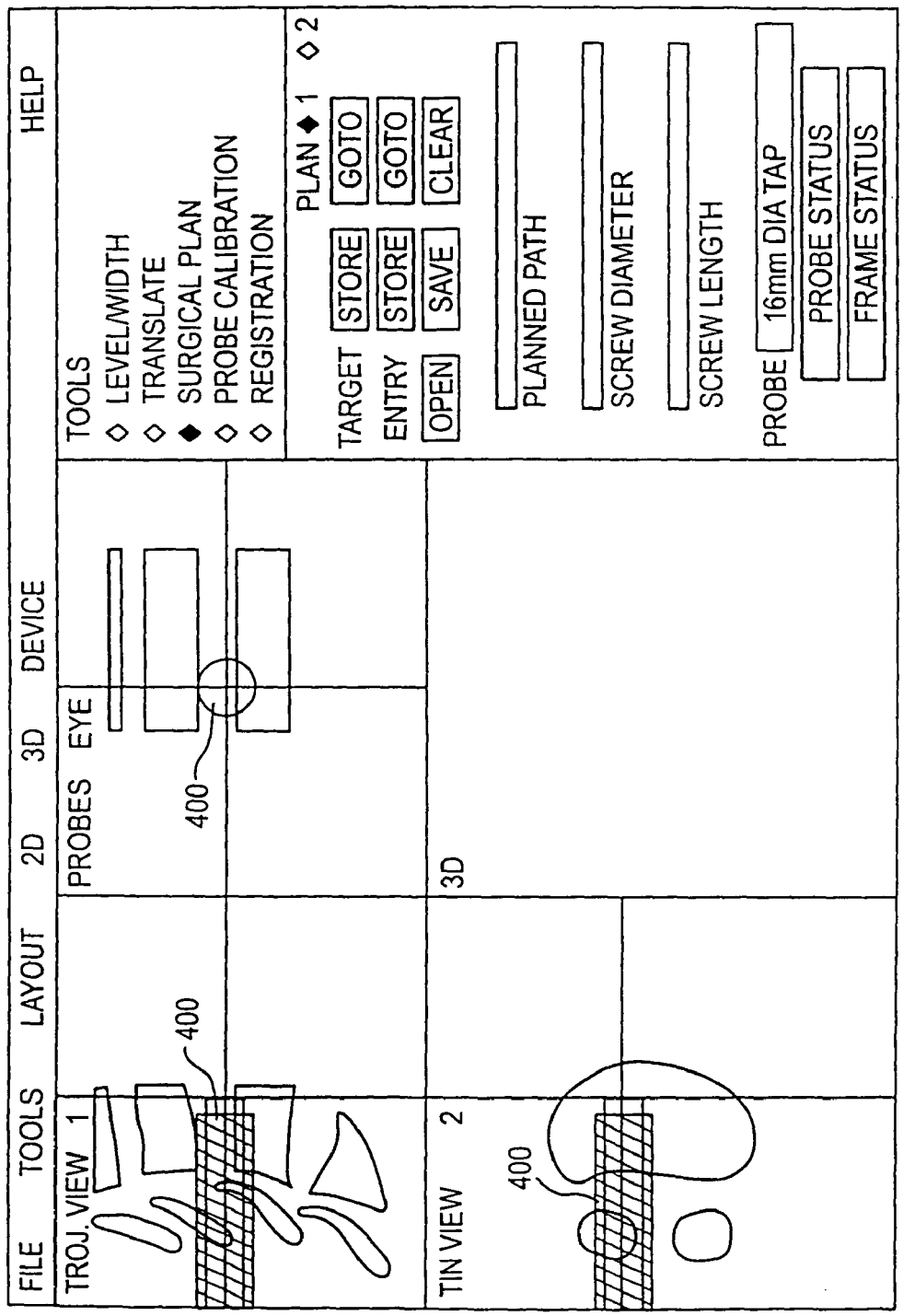
FIG. 7 depicts an image on a display screen produced in association with the guide, a tap passing through the guide, and surgical navigation system in accordance with another preferred embodiment of the present invention.

FIG. 7 depicts tap 400 being inserted through guide 130. The final position of tap 400 remains on the screen for reference by the surgeon. The diameter of tap 400 is entered into the computer or selected from a programmed menu.

Figure 8:
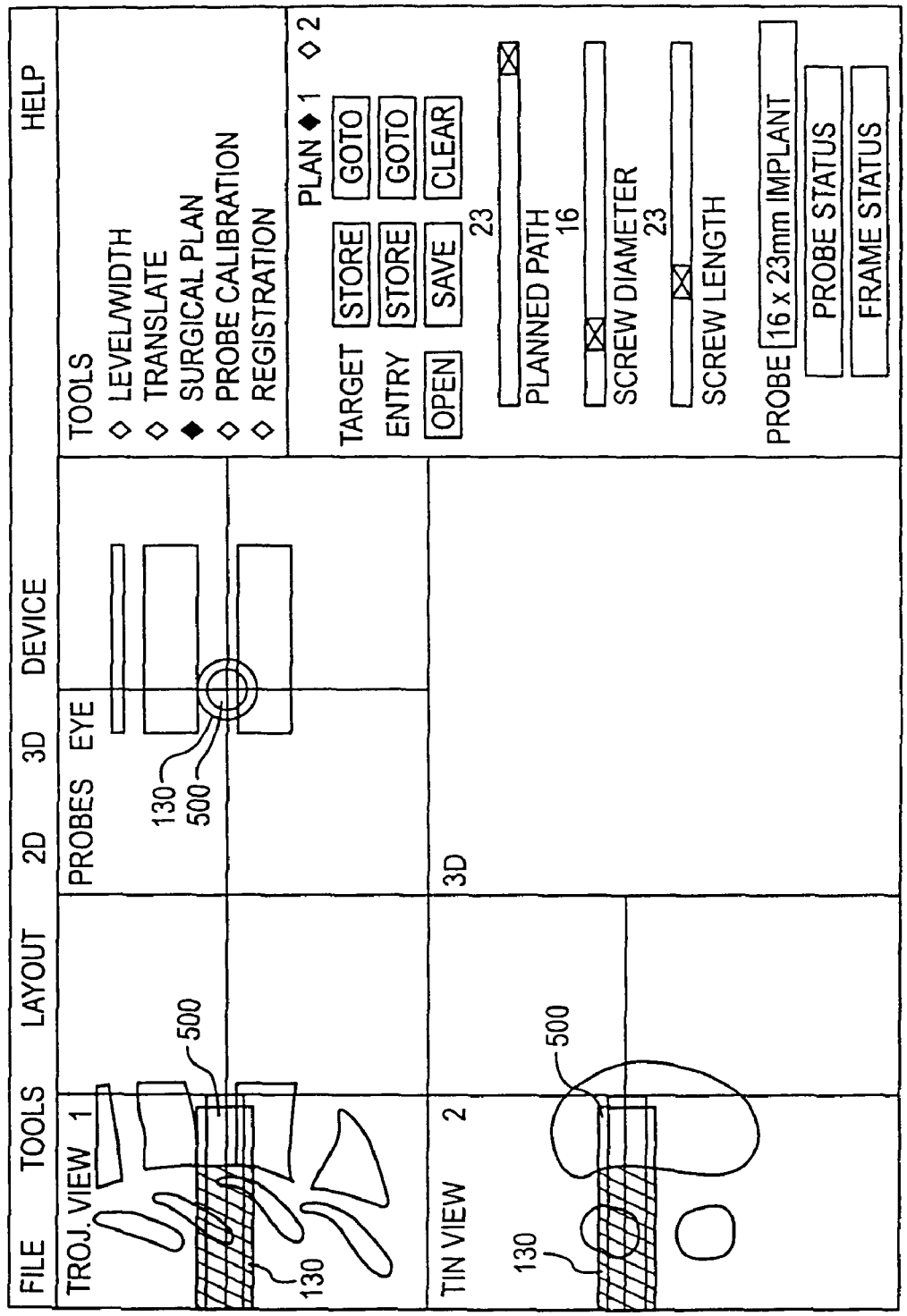
FIG. 8 depicts an image on a display screen produced in association with the guide, an implant passing through the guide, and surgical navigation system of yet another preferred embodiment of the present invention.

FIG. 8 shows a display representing the location and depth of implant 500 after insertion through guide 130. The final position of implant 500 remains on the screen for reference by the surgeon. Both the tip and tail of implant 500 is visible on the screen. The diameter and length of implant 500 is preferably entered into the computer or selected from a programmed menu.

By entering the dimensions of implant 500 into the computer or by selecting an implant size from a programmed menu and by having the geometric configuration of inserter 420 in the computer, the display can show the implant in relation to the adjacent vertebrae by knowing the position of the inserter and thereby knowing the position of a rigidly attached implant 500. In this manner, one can keep track of implant 500 or any other device of known dimension attached to a tool of known dimension having an emitter array attached thereto. By providing an emitter array on a tool of know dimension and tracking its position, the position of another device of known dimension rigidly attached to the tool can also be determined with certainty. Thus, the implant or other device can be displayed on the navigation system monitor without need for a separate emitter on the attached device.

Having described the preferred embodiment of the guide used in the present system, the method of using this apparatus to practice the invention will now be described. The operation of a surgical navigating system is generally well known and is described in PCT/US95/12894. The first step is to identify the location of the spine using computer-aided image guided surgical navigation methods.

A reference array 120 is rigidly attached to the vertebrae of interest. The attachment means can be a clamp, screw, or any other means. The reference array can be attached to a spinous process, for example, in a posterior case or to the anterior body in an anterior case. The array can be mounted percutaneously from a minimally invasive technique. Once the reference array is attached, the body of interest must be registered to the image data in the computer controlled surgical navigation system. This can be accomplished in many different ways. In an open or endoscopic case, points on the bone can be physically touched with a tracked pointer. For a percutaneous technique, points on a fiducial array which was attached to the body before the scan can be touched, or points on Fluoroscopic or Ultrasonic images can be identified. The invention may be used with any registration technique. The invention may also be used with any surgical technique (i.e. posterior, anterior, laparoscopic, anterior endoscopic, etc.)

Once the reference 120 is placed on the patient and the anatomy is registered with the computer system, guide 130 can be tracked in space relative to the spine in the surgical navigation system without further surgical exposure of the spine. The position of guide 130 is determined by the user stepping on a foot pedal 116 to energize the emitter array 190. The emitters 195 generate infrared signals to be picked up by camera digitizer array 110 and triangulated to determine the position of guide 130. The relative position of the body part, such as the spinal process is determined in a similar manner, through the use of similar emitters 122 mounted on the reference frame 120 in mechanical communication with the spinal segment. As is well known in this art and described in PCT/US95/12894, based upon the relative position of the spinal segment and guide 130 (such as by touching a known reference point) the computer would illustrate a preoperative scan—such as the proper CAT scan slice—on the screen of monitor 106 which would indicate the position of guide 130 and the spinal segment. It is also understood that passive as well as active tracking techniques can be used throughout.

After the spinal elements are registered in the spine, a guide can be properly oriented so that disc and bone may be removed through the guide to form a properly oriented implantation space into which an artificial implant or bone dowel may be inserted.

In addition, the invention further comprises a method for performing spinal surgery with a guide used to provide protected access across a spinal disc and into adjacent vertebrae to prepare an implantation space. The method comprises the following steps: contacting one end of the guide having at least one electrically energizable energy emitter array attached thereto to the adjacent vertebra; employing a surgical navigation system with a computer controller and a digitizer array for communicating with the energy emitter of the guide; positioning the guide in three dimensional space relative to a known reference point; and forming the implantation space through the guide across the disc space and into a portion of each of the adjacent vertebrae.

In another aspect, the method includes, the step of generating a display of the position of the guide. The generating step preferably displays the location of the guide relative to the adjacent vertebrae to provide a view of the axial orientation of the guide relative to each vertebra and/or relative to the adjacent vertebrae. The generating step may also display the location of the guide relative to the adjacent vertebrae to provide a cross-sectional view of the guide relative to one of an anterior or posterior view of the adjacent vertebrae. The generating step may also display the location of the guide relative to the adjacent vertebrae to provide a cross-sectional view of the guide in the sagittal and coronal planes or in planes relative to the current trajectory of the guide.

The method may also include the step of emitting a signal from an emitter attached to the guide which is received by an apparatus representatively indicating that signal on a visual display. A preferred method of the present invention also includes the step of implanting one of an artificial implant and a bone dowel into the implantation space.

It will be apparent to those skilled in the art that various modifications and variations can be made in the present invention and in construction of this guide in association with a surgical navigation system without departing from the scope or spirit of the invention. Other embodiments of the invention will be apparent to those skilled in the art from consideration of the specification and practice of the invention disclosed herein. It is intended that the specification and examples be considered as exemplary only.

What is claimed is:

1. A system for use in performing surgery to prepare an implantation space in at least one bone, said system comprising:
    a guide having an elongated wall configured to engage the at least one bone for use in preparing the implantation space, said guide defining an elongated passage extending through said guide for use in forming the implantation space;
    a tool configured to be inserted into said passage in said guide for use in performing the surgery, said tool including a first tracking device attached to said tool for use in identifying a position of said tool relative to at least one of said guide or said at least one bone; and
    a computer controlled surgical navigation system having a position tracking device configured to track positions of said tool relative to a known reference point, wherein at least one of an orientation or a depth of said tool are determined upon tracking said first tracking device; a second tracking device separately attached to said guide for use in identifying a position of said guide relative to at least one of the at least one bone or said tool; wherein said computer controlled surgical navigation system having the position tracking device is configured to track positions of both said tool and said elongated guide based on said first tracking device and said second tracking device, respectively.

2. The system as defined in claim 1 wherein said position tracking device is selected from a group of position tracking devices comprising: acoustic, magnetic, electromagnetic, radiologic, light emitting devices and micropulsed radar systems.

3. The system as defined in claim 1 wherein said guide is configured to be impacted to engage and penetrate the at least one bone.

4. The system as defined in claim 1 wherein said first and second tracking devices are active tracking devices selected from a group comprising: acoustic, magnetic, electromagnetic, radiologic, light emitting devices and micropulsed radar systems.

5. The system as defined in claim 1 wherein said first and second tracking devices are passive tracking devices having reflective surfaces.

6. The system as defined in claim 1 wherein said tool is selected from a group comprising: a distractor, a tap, an inserter and a reamer.

7. The system as defined in claim 1 wherein said guide is operable configured to engage a pair of adjacent vertebrae.

8. The system as defined in claim 7 wherein said tool is an inserter configured to insert at least one of an implant or a bone dowel in the at least one bone and wherein said first tracking device is used for identifying a position of at least one of the implant or the bone dowel.

9. The system as defined in claim 8 wherein said computer controlled surgical navigation system displays a position of said inserter and displays at least one of the implant or the bone dowel on an end of said inserter based on a geometrical configuration of said inserter and of at least one of the implant or the bone dowel attached to said inserter being entered into said computer controlled surgical navigation system.

10. The system as defined in claim 1 wherein said guide having said second tracking device is used as a dynamic reference during the surgery.

11. A system for use in performing surgery to prepare an implantation space in at least one bone, said system comprising:
    a guide configured to engage the at least one bone for use in preparing the implantation space, said guide defining a passage extending through said guide for use in forming the implantation space;
    a tool configured to be inserted into said passage in said guide for use in performing the surgery, said tool including a first tracking device attached to said tool for use in identifying a position of said tool relative to at least one of said guide or said at least one bone; and
    a computer controlled surgical navigation system having a position tracking device configured to track positions of said tool relative to a known reference point, wherein at least one of an orientation or a depth of said tool are determined upon tracking said first tracking device;
    wherein said guide includes an extension configured to engage and penetrate a spine defined at least in part by the at least one bone; wherein said guide having a second tracking device can be used as a dynamic tracking device during the surgery.

12. The system as defined in claim 11 wherein said guide includes extensions extending from a first end configured to engage and penetrate the at least one bone.

13. A system for use in performing surgery to prepare an implantation space in at least one bone, said system comprising:
- an elongated guide tube configured to engage the at least one bone for use in preparing the implantation space, said elongated guide tube defining an elongated passage extending through said elongated guide tube for use in forming the implantation space;
- a tool configured to be inserted into said elongated passage in said elongated guide tube for use in performing the surgery, said tool including a first tracking device attached to said tool for use in identifying a position of said tool relative to at least one of said elongated guide tube or said at least one bone; and
- a computer controlled surgical navigation system having a position tracking device configured to track positions of said tool relative to a known reference point, wherein at least one of an orientation or a depth of said tool are determined upon tracking said first tracking device; a second tracking device separately attached to said elongated guide tube for use in identifying a position of said guide relative to at least one of the at least one bone or said tool;
- wherein said tool is an inserter configured to insert at least one of an implant or a bone dowel in the at least one bone and wherein said first tracking device is used for identifying a position of at least one of the implant or the bone dowel;
- wherein said computer controlled surgical navigation system displays a position of said inserter and displays at least one of the implant or the bone dowel on an end of said inserter based on a geometrical configuration of said inserter and of at least one of the implant or the bone dowel attached to said inserter being entered into said computer controlled surgical navigation system.

14. The system of claim 13, wherein said computer controlled surgical navigation system is configured to track both the first tracking device and the second device and, based on tracking both the first tracking device and the second device, said computer controlled surgical navigation system displays the at least one of the implant or the bone dowel on an end of said inserter.

* * * * *